(12) United States Patent
Burbank

(10) Patent No.: US 10,631,858 B2
(45) Date of Patent: Apr. 28, 2020

(54) STAPLER WITH CABLE-DRIVEN ADVANCEABLE CLAMPING ELEMENT AND DISTAL PULLEY

(71) Applicant: Intuitive Surgical Operations, Inc., Sunnyvale, CA (US)

(72) Inventor: William A. Burbank, Sandy Hook, CT (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 419 days.

(21) Appl. No.: 15/433,101

(22) Filed: Feb. 15, 2017

(65) Prior Publication Data

US 2017/0265865 A1  Sep. 21, 2017

Related U.S. Application Data

(60) Provisional application No. 62/309,824, filed on Mar. 17, 2016.

(51) Int. Cl.
| | |
|---|---|
| *A61B 17/072* | (2006.01) |
| *A61B 34/00* | (2016.01) |
| *A61B 34/37* | (2016.01) |
| *A61B 90/00* | (2016.01) |
| *A61B 17/29* | (2006.01) |

(52) U.S. Cl.
CPC ........ *A61B 17/07207* (2013.01); *A61B 34/37* (2016.02); *A61B 34/71* (2016.02);
(Continued)

(58) Field of Classification Search
CPC . A61B 17/07207; A61B 90/361; A61B 34/37; A61B 34/71; A61B 2017/2937;
(Continued)

(56) References Cited

U.S. PATENT DOCUMENTS

| | | | | |
|---|---|---|---|---|
| 5,478,003 A | * | 12/1995 | Green | A61B 17/07207 227/176.1 |
| 5,711,472 A | * | 1/1998 | Bryan | A61B 17/07207 227/175.1 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Hemant Desai
*Assistant Examiner* — Christopher Robin Kim
(74) *Attorney, Agent, or Firm* — Schwegman Lundberg & Woessner, P.A.

(57) ABSTRACT

A surgical tool is provided comprising: a jaw assembly that includes a first and second elongated jaws each having a proximal end and a distal end, wherein the proximal end of the first jaw is mounted to be rotatable about a pivot axis between an open position and a closed position; first parallel side edges secured to the first jaw that extend parallel to a longitudinal first axis of the first jaw; second parallel side edges secured to the second jaw that extend parallel to a longitudinal second axis of second jaw; a slider beam that includes a cross-beam portion sized to slidably fit between the first parallel side edges and between the second parallel side edges, a first transverse beam configured to slidably engage surfaces of the first parallel side edges facing away from the second jaw, and a second transverse beam configured to slidably engage surfaces of the second parallel side edges facing away from the first jaw; a pulley rotatably mounted to the distal end of the first jaw; and a first slider cable secured to one side of the first transverse beam, the first slider cable extending about the pulley and past another side of the first transverse beam to the proximal end of the first jaw.

14 Claims, 20 Drawing Sheets

(52) U.S. Cl.
CPC .. *A61B 90/361* (2016.02); *A61B 2017/07257* (2013.01); *A61B 2017/07278* (2013.01); *A61B 2017/07285* (2013.01); *A61B 2017/2927* (2013.01); *A61B 2017/2937* (2013.01); *A61B 2090/371* (2016.02)

(58) Field of Classification Search
CPC .. A61B 2017/07257; A61B 2017/2927; A61B 2090/371; A61B 2017/07278; A61B 2017/07285
See application file for complete search history.

(56) References Cited

U.S. PATENT DOCUMENTS

| | | | | |
|---|---|---|---|---|
| 6,250,532 | B1* | 6/2001 | Green | A61B 17/07207 227/175.1 |
| 2005/0006432 | A1* | 1/2005 | Racenet | A61B 17/07207 227/176.1 |
| 2005/0103819 | A1* | 5/2005 | Racenet | A61B 17/07207 227/175.1 |
| 2008/0035701 | A1* | 2/2008 | Racenet | A61B 17/07207 227/176.1 |
| 2012/0241503 | A1* | 9/2012 | Baxter, III | A61B 17/0643 227/176.1 |
| 2012/0292367 | A1* | 11/2012 | Morgan | A61B 17/072 227/175.1 |
| 2014/0350570 | A1* | 11/2014 | Lee | A61B 17/2909 606/130 |
| 2015/0150635 | A1* | 6/2015 | Kilroy | B25J 15/0286 606/130 |
| 2015/0282809 | A1* | 10/2015 | Shelton, IV | A61B 17/068 227/176.1 |
| 2016/0166253 | A1* | 6/2016 | Knodel | A61B 17/07207 227/175.1 |
| 2018/0008265 | A1* | 1/2018 | Hatanaka | A61B 17/0682 |

* cited by examiner

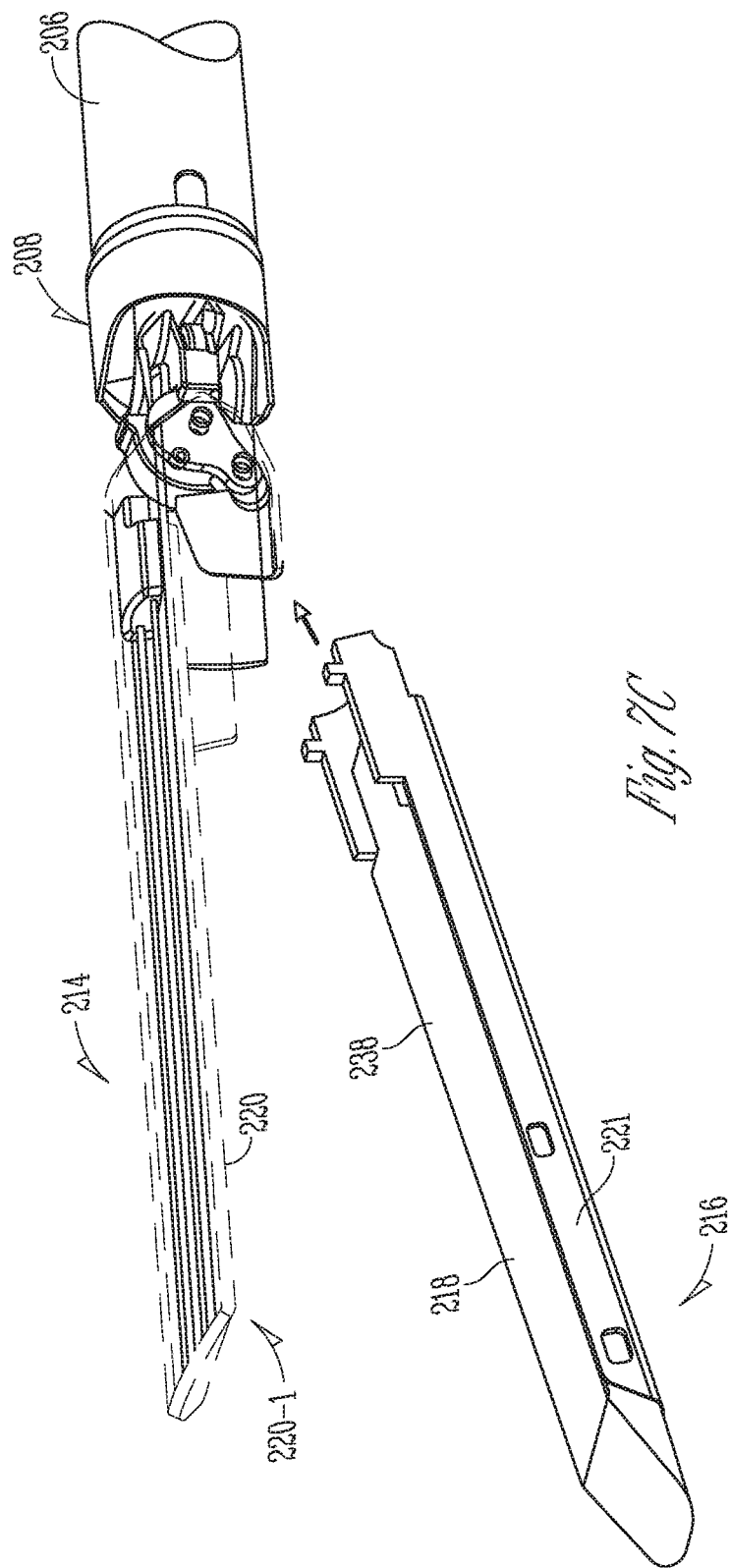

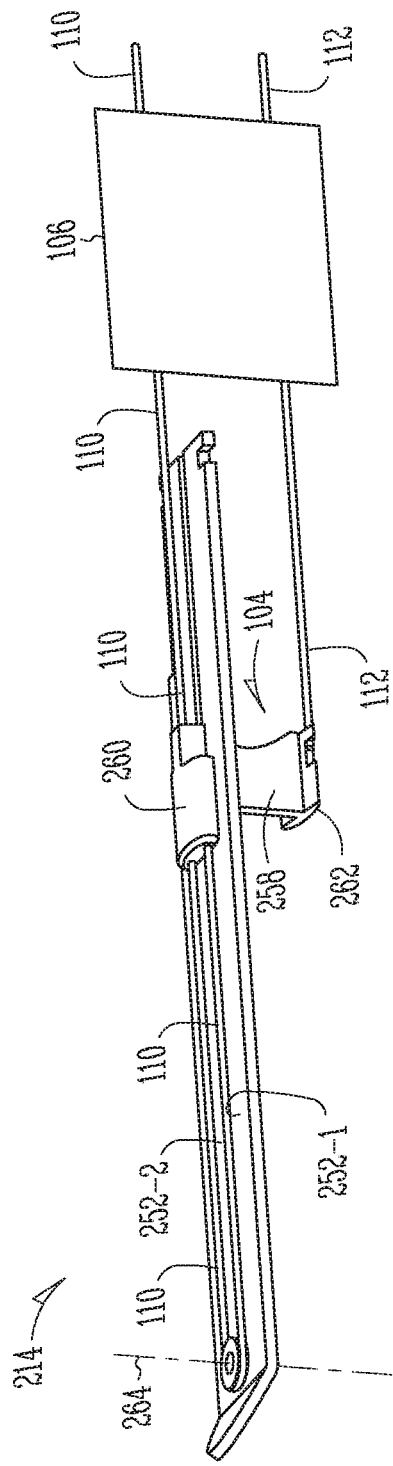
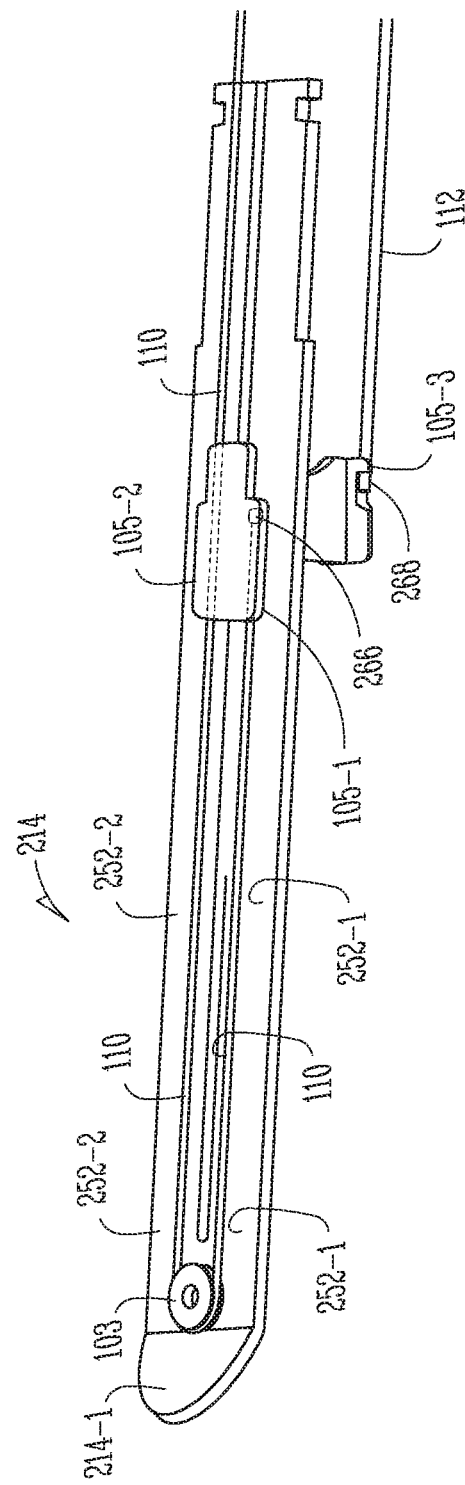

STAPLER WITH CABLE-DRIVEN ADVANCEABLE CLAMPING ELEMENT AND DISTAL PULLEY

RELATED APPLICATIONS

This patent application claims priority to and the benefit of the filing date of U.S. Provisional Patent Application 62/309,824, entitled "STAPLER WITH CABLE-DRIVEN ADVANCEABLE CLAMPING ELEMENT AND DISTAL PULLEY" filed Mar. 17, 2016, which is incorporated by reference herein in its entirety.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

Minimally invasive teleoperated surgical systems have been developed to increase a surgeon's dexterity when working on an internal surgical site, as well as to allow a surgeon to operate on a patient from a remote location (outside the sterile field). In a teleoperated surgical system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the teleoperated surgical system can provide mechanical actuation and control of a variety of surgical instruments or tools having end effectors that perform various functions for the surgeon, for example, holding or driving a needle, grasping a blood vessel, dissecting tissue, stapling tissue, or the like, in response to manipulation of the master input devices.

SUMMARY

A surgical instrument includes a jaw assembly that includes first and second elongated jaws each having a proximal end and a distal end. The proximal end of the first jaw is mounted to be rotatable about a pivot axis between an open position and a closed position. First parallel side edges are secured to the first jaw and extend parallel to a longitudinal first axis of the first jaw. Second parallel side edges are secured to the second jaw and extend parallel to a longitudinal second axis of the second jaw. A slider beam includes a cross-beam portion sized to slidably fit between the first parallel side edges and between the second parallel side edges. The slider beam also includes a first transverse beam configured to slidably engage surfaces of the first parallel side edges facing away from the second jaw and a second transverse beam configured to slidably engage surfaces of the second parallel side edges facing away from the first jaw. A pulley is rotatably mounted to the distal end of the first jaw. A first slider cable is secured to the first transverse beam, the first slider cable and extends from a distal side of a portion of the first transverse beam that engages one of the first parallel side edges, extends about the pulley, extends through a channel formed in a portion of the first transverse beam that engages another of the first parallel side edges, and extends to the proximal end of the first jaw. In some embodiments, a second slider cable is secured to one of the first and second transverse beams and extends between the second transverse beam and the proximal end portion of the second jaw.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 7C is an illustrative perspective view of the surgical tool assembly showing the detachable stationary second jaw detached from the rest of the assembly, in accordance with some embodiments.

FIG. 12 is an illustrative side perspective view of the first jaw showing a jaw-mounted pulley and a first transverse beam portion of a cable driven slider beam of the embodiment of FIGS. 7A-7C, in accordance with some embodiments.

FIG. 13 is an illustrative perspective view of the first jaw of FIG. 12 showing tubular guide channels formed in first and second transverse beam portions of the slider member of FIGS. 9A-C, in accordance with some embodiments.

DESCRIPTION OF EMBODIMENTS

Figure 1:
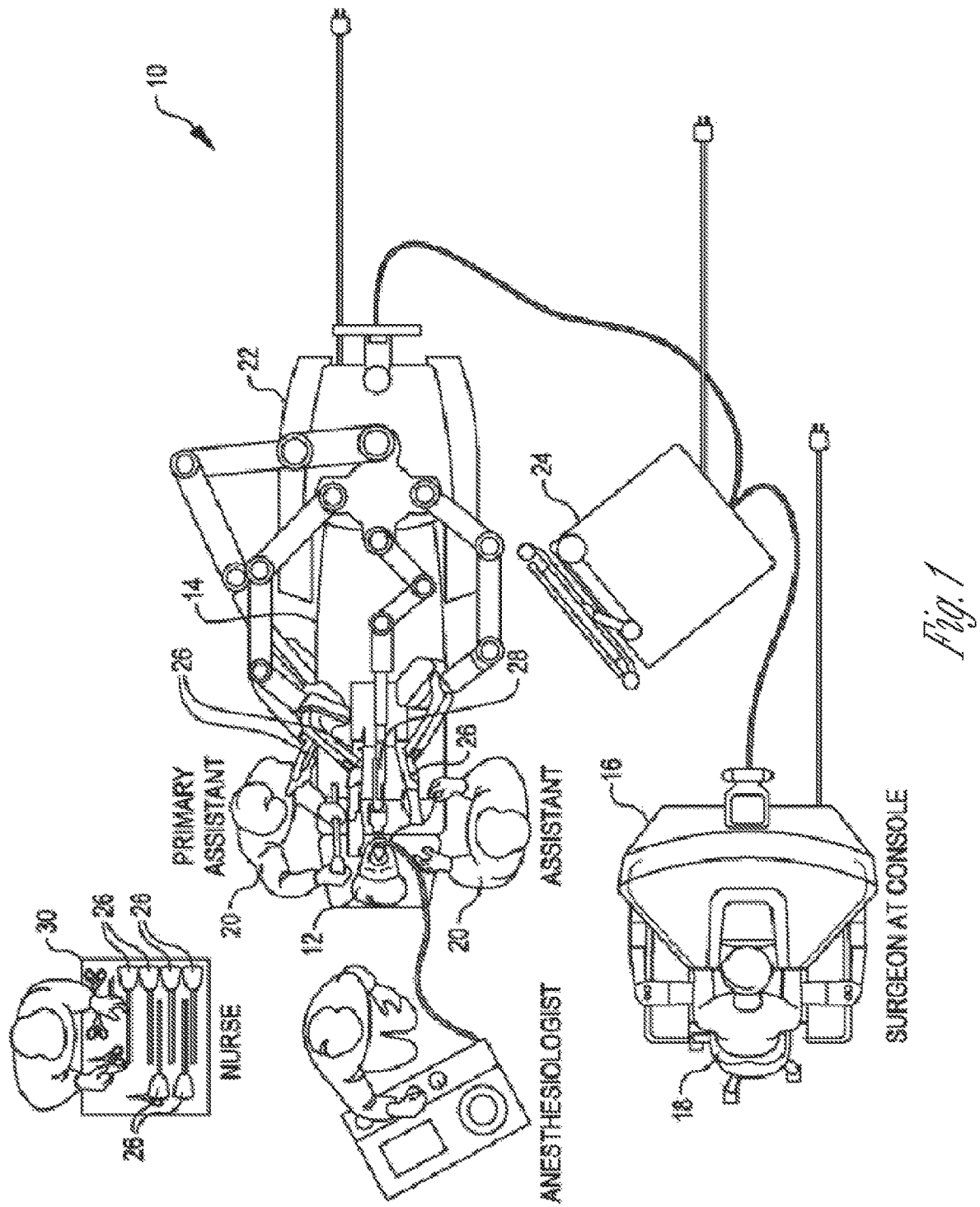
FIG. 1 is an illustrative plan view illustration of a teleoperated surgical system in accordance with some embodiments.

The following description is presented to enable any person skilled in the art to create and use a cable driven I-beam for use in surgery. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Thus, the inventive subject matter is not intended to be limited to the embodiments shown, but is to be accorded the widest scope consistent with the principles and features disclosed herein.

Referring now to the drawings, in which like reference numerals represent like parts throughout the several views, FIG. 1 is an illustrative plan view of a teleoperated surgical system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The teleoperated surgical system 10 can further include a Patient Side Cart 22 and an Electronics Cart 24. The Patient Side Cart 22 can manipulate at least one removably coupled tool assembly 26 (hereinafter also referred to as a "tool") through a minimally invasive incision in the body of the Patient 12 while the Surgeon 18 views the surgical site through the Console 16. An image of the surgical site can be obtained by an imaging device 28 (also called "endoscope 28"), such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors.

Figure 2:
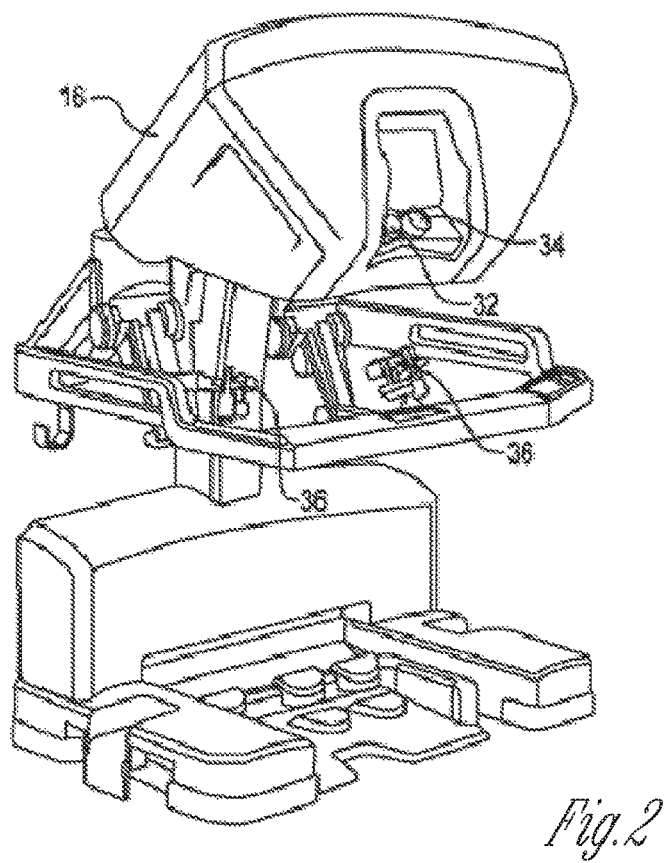
FIG. 2 is an illustrative perspective view of the Surgeon's Console in accordance with some embodiments.

FIG. 2 is an illustrative perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

Figure 3:
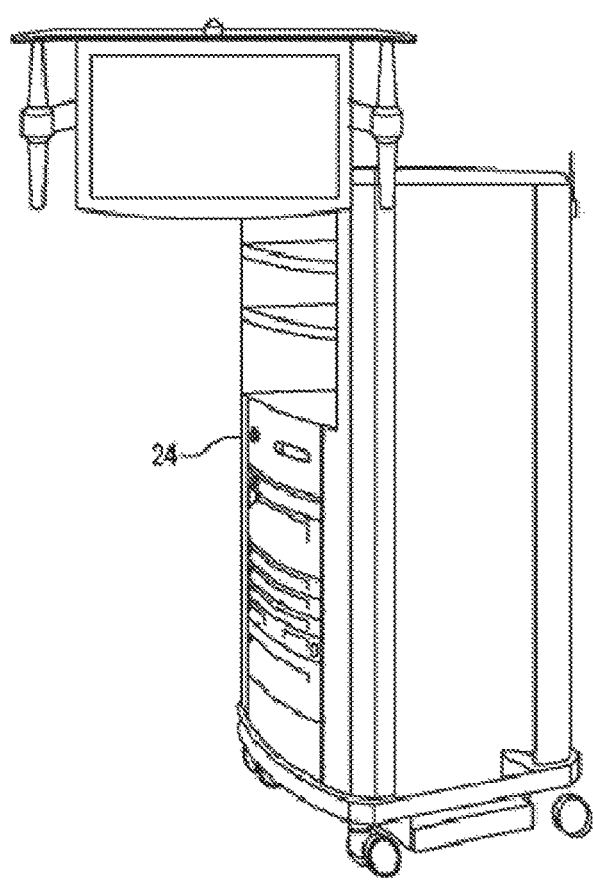
FIG. 3 is an illustrative perspective view of the Electronics Cart in accordance with some embodiments.

FIG. 3 is an illustrative perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope.

Figure 4:
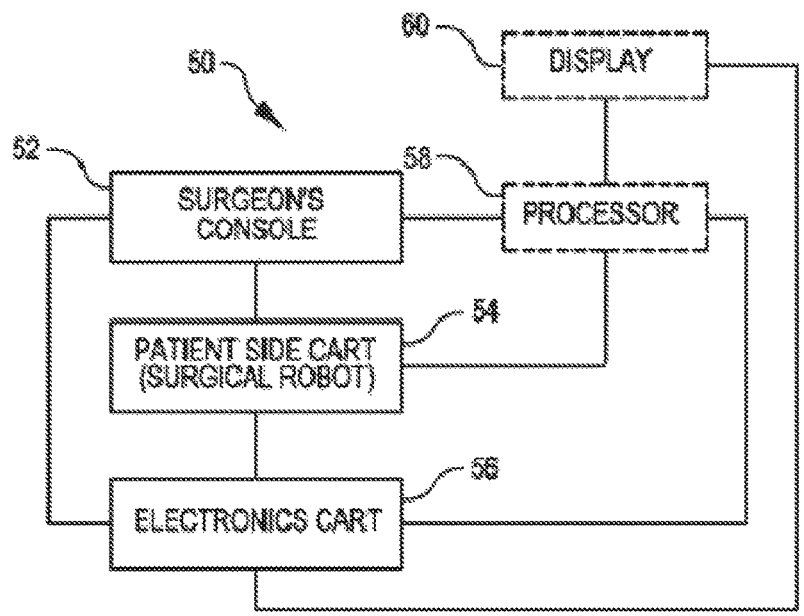
FIG. 4 is an illustrative bock diagram diagrammatically representing functional relationships among components of a teleoperated surgery system in accordance with some embodiments.

FIG. 4 is an illustrative bock diagram diagrammatically representing functional relationships among components of a teleoperated surgery system 50 (such as system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
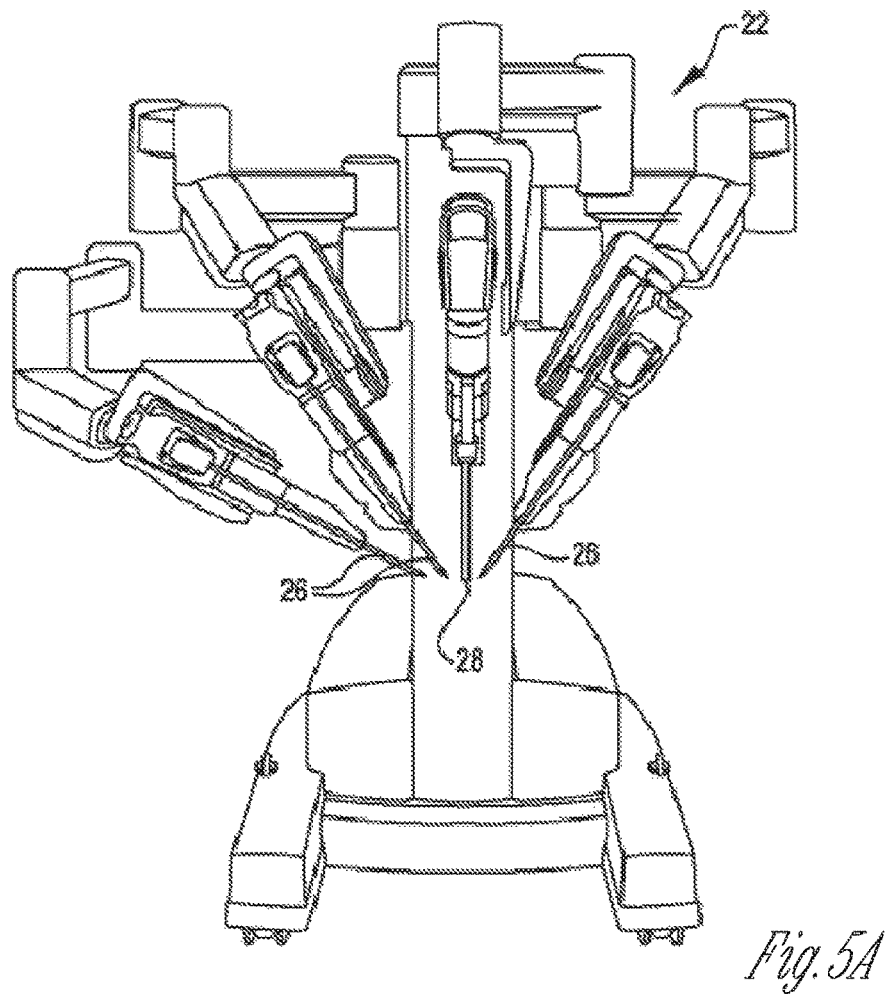
FIGS. 5A-5B are illustrative drawings showing a Patient Side Cart and a surgical tool respectively in accordance with some embodiments.
Figure 5B:
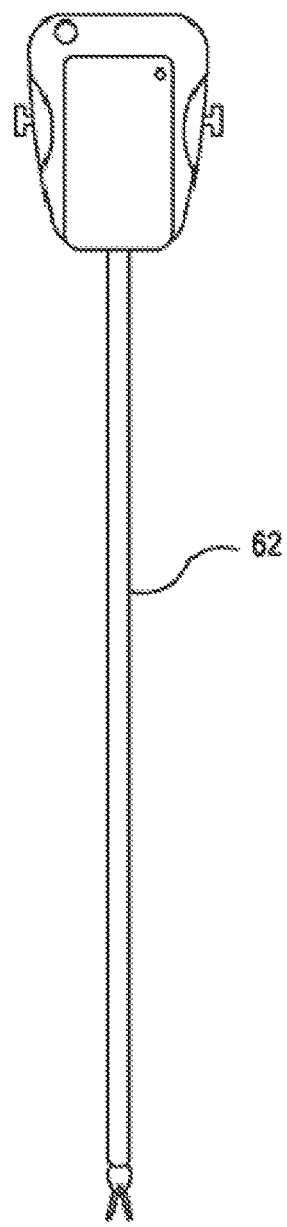

FIGS. 5A-5B are illustrative drawings showing a Patient Side Cart 22 and a surgical tool 62, respectively in accordance with some embodiments. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by teleoperated mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Figure 6:
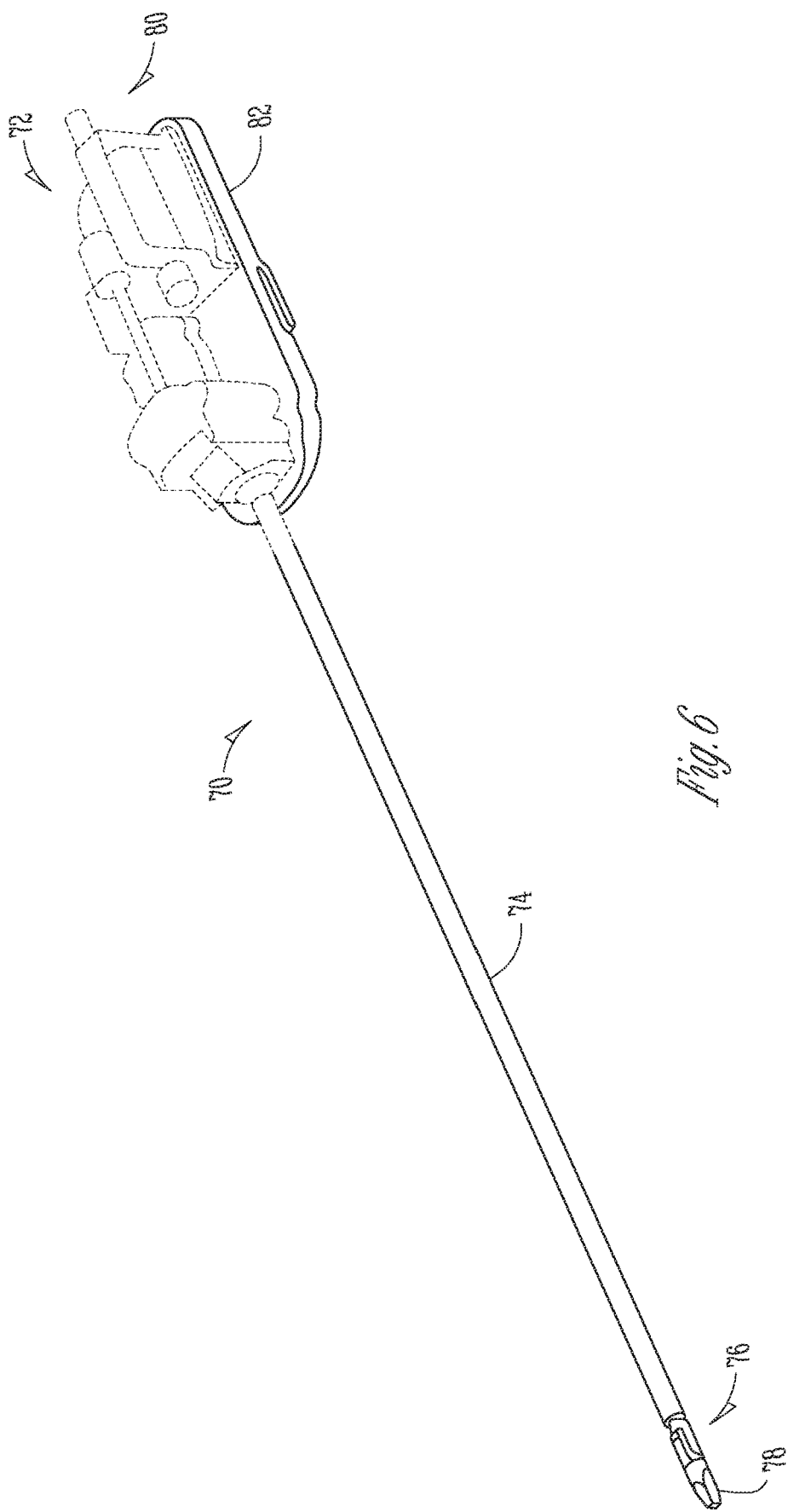
FIG. 6 is an illustrative drawing showing an example surgical tool in accordance with some embodiments.

FIG. 6 is an illustrative drawing showing an example surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with drive shafts that are disposed within the instrument shaft 74. The drive shafts are drivingly coupled with the end effector 76.

Figure 7A:
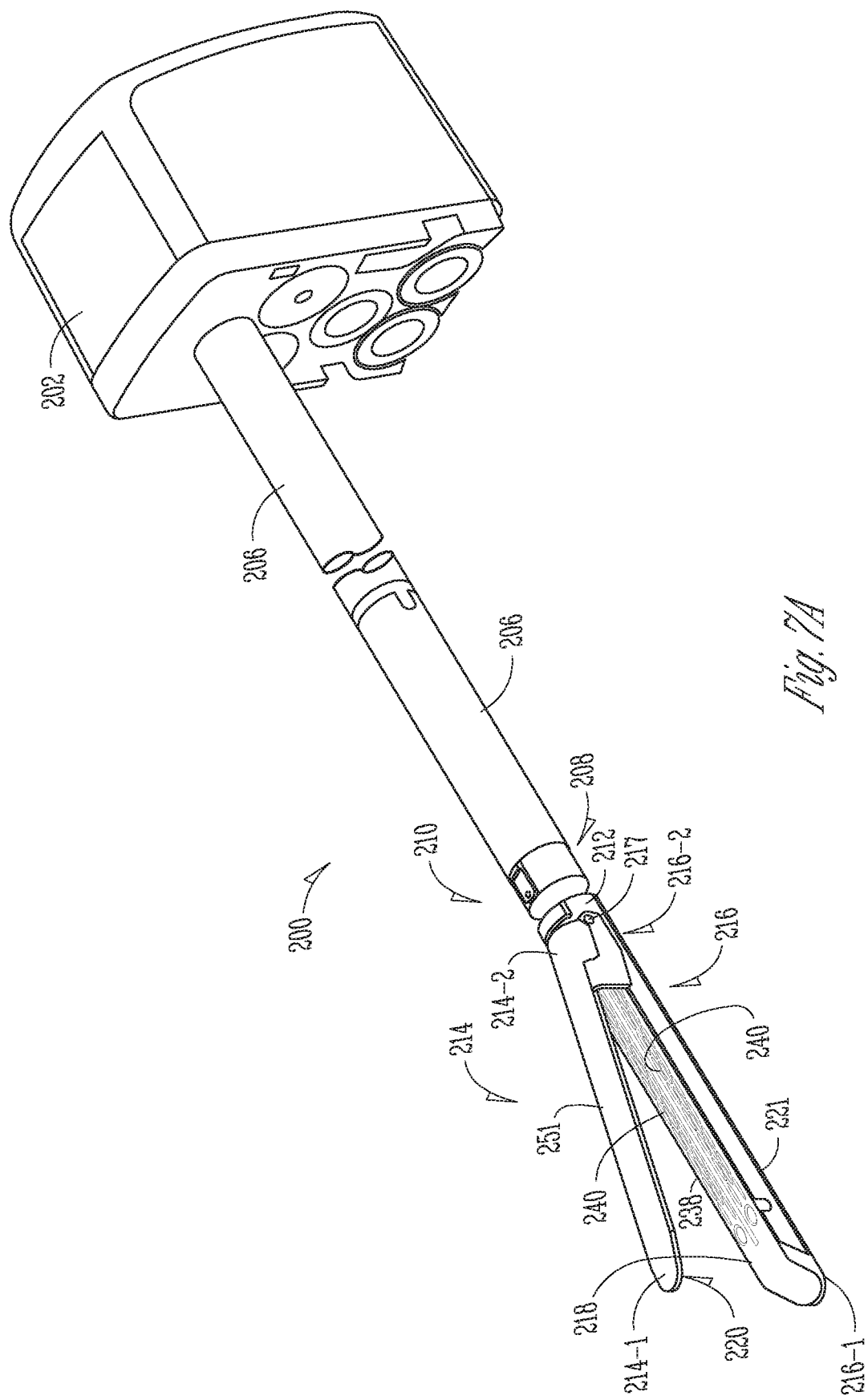
FIG. 7A is an illustrative perspective drawing of a surgical tool assembly in accordance with some embodiments.

FIG. 7A is an illustrative perspective drawing of a surgical tool assembly 200 with a jaw assembly 210 that includes first and second jaws 214, 216 shown in an open position in accordance with some embodiments. The tool assembly 200 includes a proximal actuation assembly 202, a main shaft 206, a two degree of freedom (2-dof) wrist 208, shown in partial cutaway, and an end effector jaw assembly 210. The jaw assembly 210 includes a base 212 coupled to a distal side of the 2-dof wrist 208, a first articulable jaw 214 and a detachable stationary second jaw 216. The first jaw 214 has a distal end 214-1 (also called "distal end portion 214-1") and a proximal end 214-2. (also called "proximal end portion 214-4"). The second jaw 216 also has a distal end 216-1 and a proximal end 216-2. In operation, the base 212 is an integral part of the proximal end 216-2 of the second jaw 216. The base 212 includes a pivot pin 217 secured between the base 212 and a proximal end of the first jaw 214, about which a proximal end of the first jaw 214 pivots to achieve opening and closing movement of the first jaw 214 relative to the second jaw 216. In an open position shown in FIG. 7A, the first jaw 214 is rotated to a position in which distal ends 214-1, 216-1 of the first and second jaws 214, 216 are spaced apart so that the jaws can be more easily maneuvered within a surgical site to encompass anatomical tissue (not shown) between them without actually clamping the tissue in place between them.

The jaw assembly 210 includes a surgical stapler in which the second jaw 216 is detachable and stationary relative to the base 212. The second jaw 216 includes an elongated stapler cartridge 218 seated within a stapler cartridge support channel 221 configured to support the cartridge 218. The stapler cartridge 218 carries fasteners, e.g., staples to be used to attach tissue during a surgical procedure. The stapler cartridge 218 defines a central longitudinal cartridge slot 238 that extends through the cartridge 218 and extends along substantially its entire length. The stapler cartridge 218 also defines multiple laterally spaced rows of staple retention slots 240 that extend longitudinally along one side of the first cartridge slot 238 and defines multiple laterally rows of spaced staple retention slots 240 that extend longitudinally along an opposite side of the first cartridge slot 238. Each staple retention slot 240 is sized to receive a staple (not shown).

In many embodiments, the actuation assembly 202 includes one or more motors (not shown) and is operatively coupled with the wrist 208 so as to selectively reorient the jaw assembly 210 relative to the main shaft 206 in two dimensions, referred to as pitch and yaw, and is operatively coupled with the jaw assembly 210 so as to actuate one or more jaw assembly features, such as rotation of the first jaw 214 about the pivot pin 217 to open and close the first jaw 214 relative to the base 212 and the second jaw 216. In accordance with some embodiments, control cables, which include cable segments coupled with hypotubes, are used to operatively couple the actuation assembly 202 with the wrist 208 and with the jaw assembly 210. The control cables are routed between the actuation assembly 202 and the wrist 208 and the jaw assembly 210 through a bore of the main shaft 206.

Figure 7B:
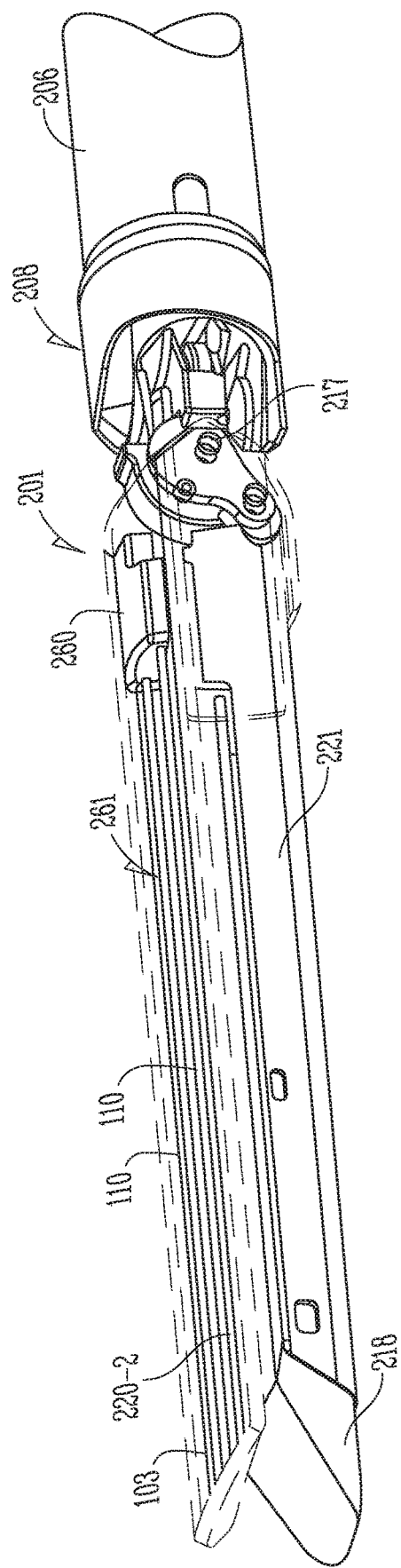
FIG. 7B is an illustrative perspective view of the surgical tool assembly showing cable control components disposed within a first jaw channel defined by an anvil and an outer first jaw cover, in accordance with some embodiments.

In a closed position shown in FIG. 7B, the first and second jaws are disposed parallel to each other spaced apart by an amount to accommodate anatomical tissue (not shown) that may be clamped between them. The first jaw 214 includes an anvil 220 having a first surface 220-1 that faces the second jaw 216 and a second surface 220-2 that faces away from the second jaw 216. In operation, staples are deformed against the anvil first surface 220-1 to staple together tissue (not shown) disposed between the first and second jaws 214, 216. An outer first jaw cover 251, shown transparent with dashed lines in FIG. 7B, overlays a back side of the anvil 220 so that the anvil second surface 220-2 and the outer first jaw cover 251 together define an enclosed first jaw channel 261 between them. A first transverse beam portion 260 of a cable driven slider beam 104, which is discussed more fully below, a jaw-mounted pulley 103 and a first cable segment 110 are shown disposed within the first jaw channel 261 in accordance with some embodiments.

FIG. 7C shows the second jaw 216 detached from the base portion 212 of the jaw assembly 210. In operation, the second jaw 216 containing a full load of staples is releasably secured to cooperate with the first anvil surface 220-1, facing the second jaw 216, so as to deform staples so as to fasten them to staple anatomical tissue (not shown) disposed between the jaws when they are in a closed position. Once the staples have been fired, the second jaw 216 with the spent cartridge 218 can be removed and may be replaced by a replacement second jaw 216 with a fully loaded stapler cartridge 218.

Figure 8:
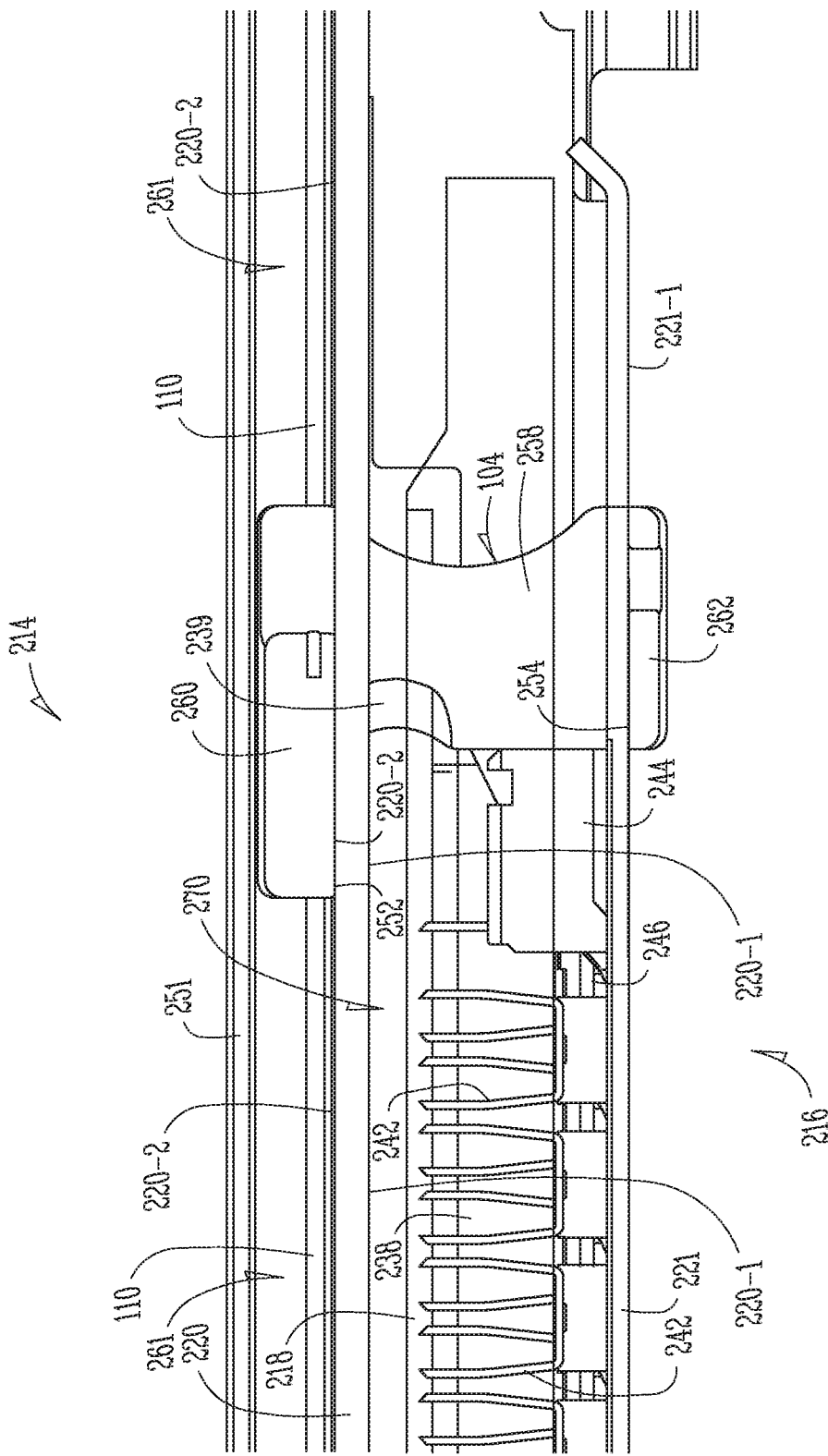
FIG. 8 is an illustrative cross-sectional side view of proximal portions of the first and second jaws of the embodiment of FIGS. 7A-7C in a closed position, in accordance with some embodiments.

FIG. 8 is an illustrative cross-sectional side view of proximal portions of the first and second jaws 214, 216 in a closed position, in accordance with some embodiments. The first and second jaws 224, 216 extend parallel to each other with a space 270 between them that is wide enough to capture and clamp tissue between them. The cartridge 218 is shown with staples 242 housed in retention the slots 240 therein. The cable driven slider beam 104 is shown having a cross-beam portion 258 having first and second transverse beam portions 260, 262 mounted on opposite ends thereof. The cross-beam portion 258 is slidably mounted within the cartridge slot 238, and the cartridge 218 disposed between the first and second transverse beam portions 260, 262.

Figure 9A:
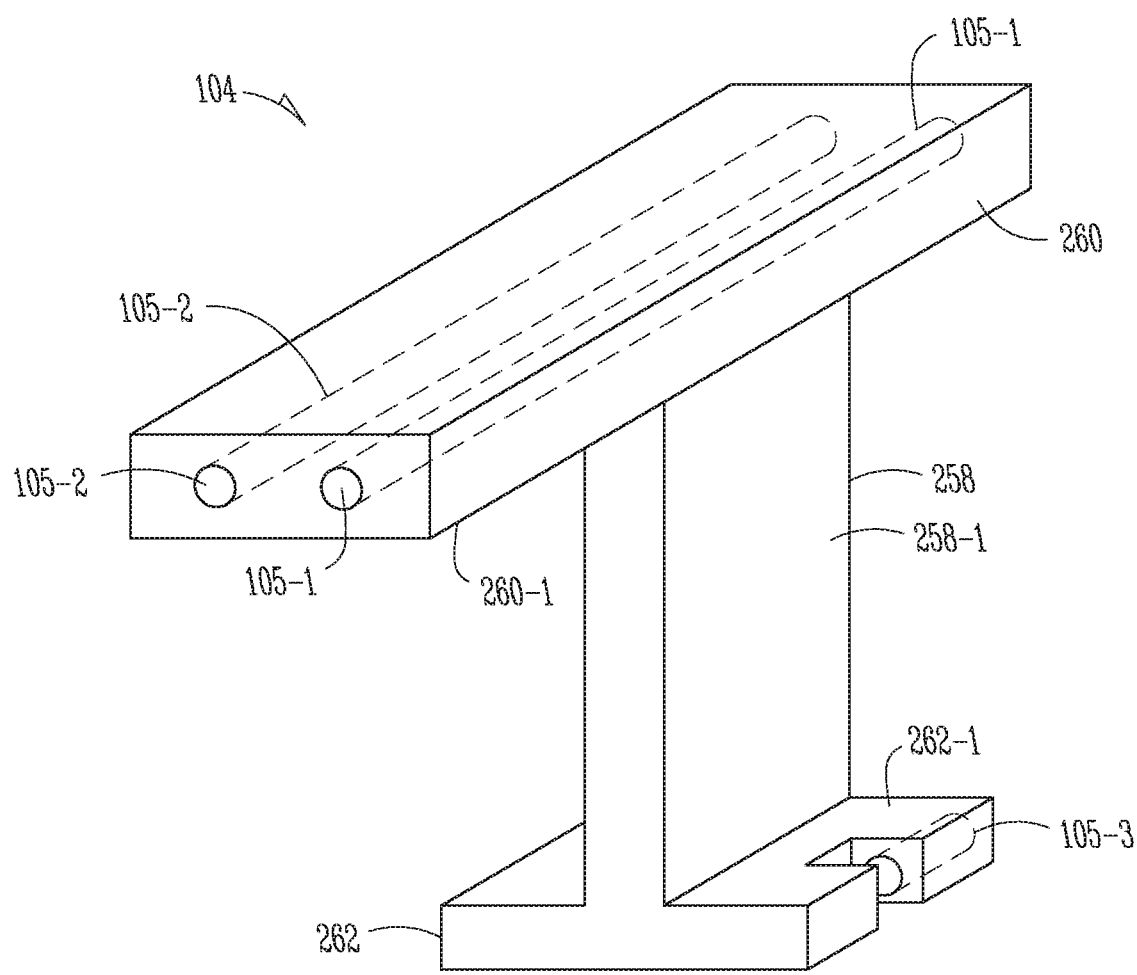
FIG. 9A is an illustrative perspective view of the slider beam of the embodiment of FIGS. 7A-7C, in accordance with some embodiments.

FIG. 9A is an illustrative perspective view of the slider beam 104 in accordance with some embodiments. The slider beam 104 has an i-beam contour that includes the cross-beam portion 258, the first transverse beam portion 260 secured to a first end of the cross-beam portion 258, and the second transverse beam 262 secured to a second end of the cross-beam 258 portion. In operation, the cross-beam portion 258 acts as a cartridge slot cam follower. As shown in FIG. 8, the cross-beam portion 258 is sized to slidably fit simultaneously within a first elongated slot 253 defined by the anvil 220 and best shown in FIG. 9 and a second elongated slot 255 defined by a bottom surface 221-1 of the cartridge support channel 221 and best shown in FIG. 10. The first transverse beam portion 260 laterally overhangs the cross-beam portion so as to define a first inward facing surface 260-1 that acts as a first jaw cam follower. The first transverse beam portion 260 also defines first and second tubular guide channels 105-1, 105-2. The second transverse beam 262 laterally overhangs the cross-beam portion so as to define a second inward facing surface 260-2 that acts as a second jaw cam follower. The first transverse beam portion 260 also defines a third tubular guide channel 105-3.

Figure 9B:
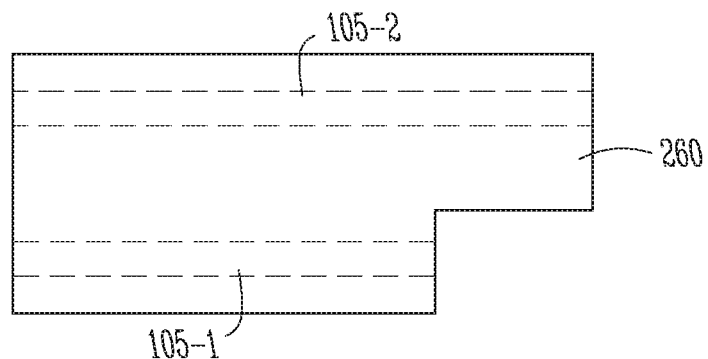
FIG. 9B is an illustrative top elevation view of the first transverse beam portion of the slider beam of the embodiment FIG. 9A, showing first and second tubular guide channels therein, in accordance with some embodiments.

FIG. 9B is an illustrative top elevation view of a first transverse beam portion 260 of the slider beam 104 showing first and second tubular guide channels 105-1, 105-2 therein in accordance with some embodiments. The first transverse beam portion 260 defines first and second co-planar, parallel tubular guide channels 105-1, 105-2, indicted by dashed lines, that are sized to permit passage of portions of the first cable segment 110, in accordance with some embodiments.

Figure 9C:
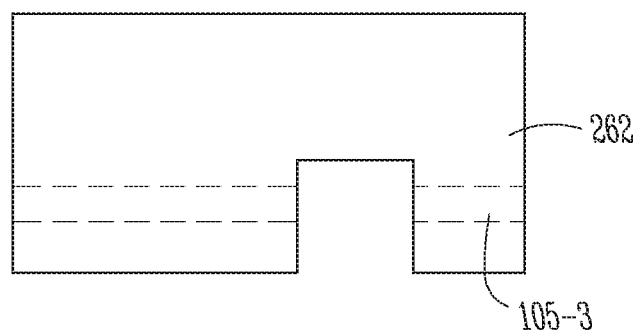
FIG. 9C is an illustrative top elevation view of the second transverse beam portion of the slider beam of FIG. 9B, showing a third tubular guide channel therein, in accordance with some embodiments.

FIG. 9C is an illustrative top elevation view of the second transverse beam portion 262 of the slider beam 104 showing a third tubular guide channels 105-3 therein in accordance with some embodiments. The second transverse beam portion 262 defines a third tubular guide channel 105-3, indicted by dashed lines, which is parallel to the first and second tubular guide channels 105-1, 105-2 and sized to permit passage of a portion of a second cable segment 112, which is discussed below. In some embodiments axes of the first and second are equally spaced apart in a transvers direction from the same side of the cross-beam portion 258.

Referring again to FIG. 8, a portion of a second surface 220-2 of the anvil 220 facing away from the second jaw 216 includes a first jaw clamping cam surface 252, which is defined by the first elongated slot 253, which is described more fully below with reference to FIG. 10. A bottom surface 221-1 of the stapler cartridge support channel structure 221 facing away from the first jaw 214 includes a second jaw clamping cam surface 254, which is defined by the second elongated slot 255, which is described more fully below with reference to FIG. 11. When the first and second jaws 214, 216 in a closed position, the first and second elongated slots, 253, 255 and the cartridge slot 238 are vertically and longitudinally aligned. The cross-beam portion 258 slider beam 104 extends through all them. The slider beam's 104 first transverse beam portion 260 slidably engages the first jaw clamping cam surface 252 defined by the first elongated slot 253. The slider beam's 104 second transverse beam 262 slidably engaging the second jaw clamping cam surface 254 defined by the second elongated slot 255.

As described more fully below, while the first and second jaws 214 216 are in a closed position, the slider beam 104 the moves longitudinally between the proximal ends 214-2, 216-2 and the distal ends 214-1, 216-1 of the first and second jaws 214, 216. During this longitudinal movement of the slider beam 104, the first transverse beam portion 260 interacts with the first jaw clamping cam surface 252, and the second transverse beam 262 interacts with the second jaw clamping cam surface 254 so as to cooperate with each other to apply a clamping force to clamp the first and second jaws 214, 216 in a substantially fixed vertical position relative to each other.

More particularly, the first and second cable segments 110, 112, shown best in FIGS. 12-13 cooperate to move the slider beam 104 between the proximal ends 214-2, 216-2 and the distal ends 214-1, 216-1 of the first and second jaws 214, 216. In accordance with some embodiments, as the slider beam 104 moves longitudinally along the length of the closed jaws, it pushes in front of it a staple pusher 244 having a distally mounted ramp structure 246 that urges fasteners 242 out from retention slots 240 into staple deforming cavities (not shown) formed within the first anvil surface 220-1 of the first jaw 214 so as to insert and fasten the staples to tissue (not shown) that can be disposed between the first and second jaws 214, 216. In some embodiments, the cross-beam portion 258 defines a knife 239 that trails behind the staple pusher 244 as it moves in a distal direction so as to cut tissue portions disposed after they have been stapled. U.S. Pat. No. 8,991,678 (filed Oct. 26, 2012) issued to Wellman et al., which is incorporated herein in its entirety by this reference, discloses a surgical stapler cartridge and its operation.

Figure 10:
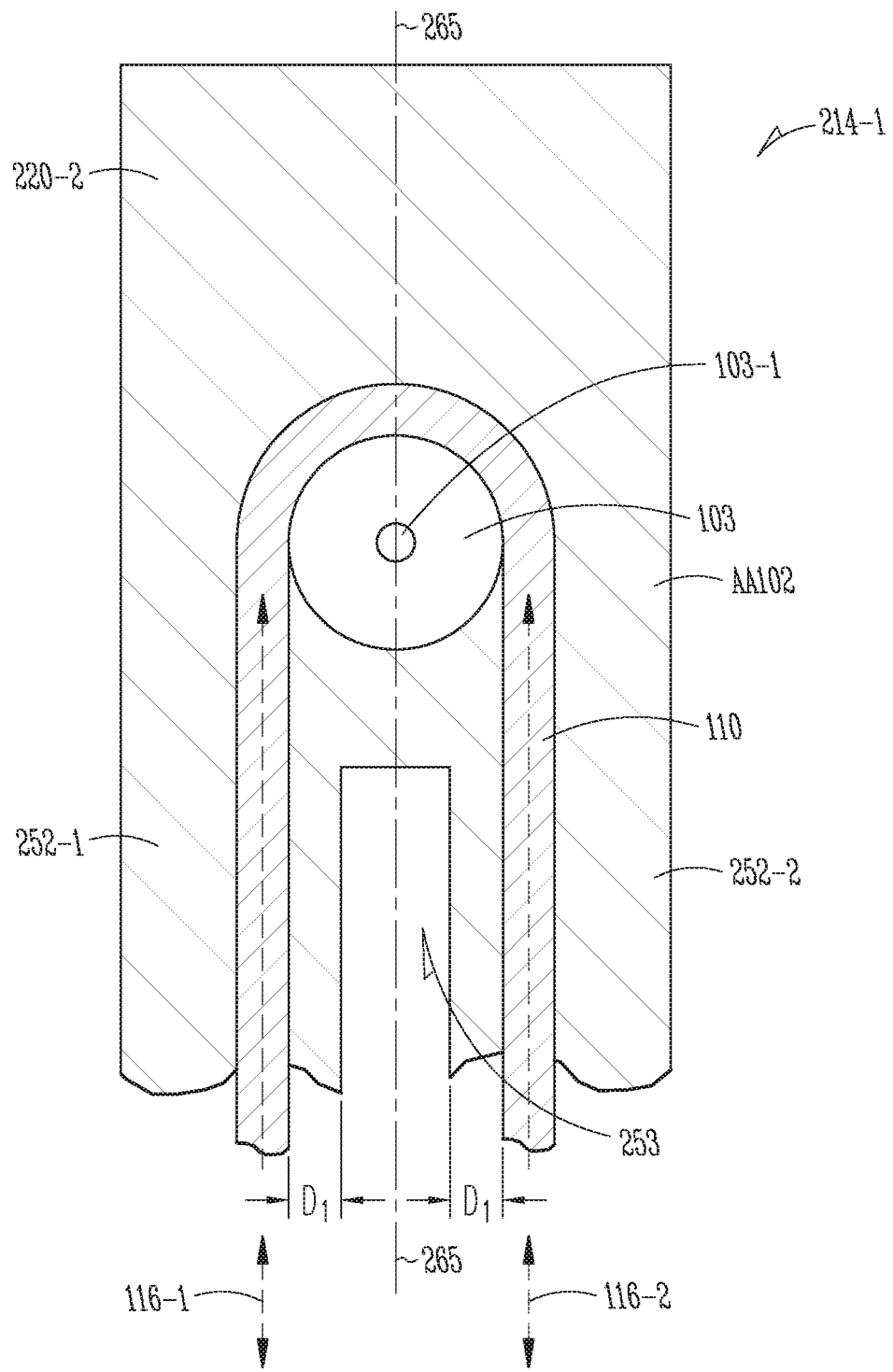
FIG. 10 is an illustrative top elevation view of the distal end portion of the first jaw of the embodiment of FIGS. 7A-7C showing arrangement of a jaw mounted pulley relative to a first elongated slot formed in the first jaw and relative to a first cable segment, in accordance with some embodiments.

FIG. 10 is an illustrative top elevation view of the distal end portion 214-1 of the first jaw 214 showing arrangement of the jaw mounted pulley 103 relative to the first elongated slot 253 formed in the anvil 220 and relative to the first cable segment 110. Arrows 116 indicate the path of movement of the first cable segment 110, which moves in two directions along the path. The outer first jaw cover 251 is shown transparent so as to reveal the components beneath it. The second surface 220-2 of the anvil 220 includes the first jaw clamping cam surface 252, which includes a first elongated clamping cam edge 252-1 and a parallel second elongated cam edge 252-2 that run on opposite sides of and parallel to the first elongated slot 253. The cross-beam portion 258 slides within the first elongated slot 253 with a first inward facing surface 260-1 of the first transverse beam portion 260 contacting the cam edges 252-1, 252-2. As explained more fully below, the pulley 103 is mounted on a distal pulley axle 103-1 that upstands from the second surface 220-2 of the anvil 220 within the first jaw channel 261. The jaw mounted pulley 103 is positioned in alignment with a center axis 265 of the first elongated slot 253. The first cable segment 110 wraps around the jaw mounted pulley such that portions of the first cable extend longitudinally along opposite sides of the first elongated slot 253. The portions of the first cable 110 extending along the opposite sides of the first elongated slot 253 are equally spaced from it by an amount $D_1$. Moreover, the portions of the first cable 110 extending along the opposite sides of the first elongated slot 253 are spaced apart in a perpendicular direction, i.e. perpendicular to a plane of the second surface 220-2, from portions of the respective first and second elongated clamping cam edges 252-1, 252-2.

Figure 11:
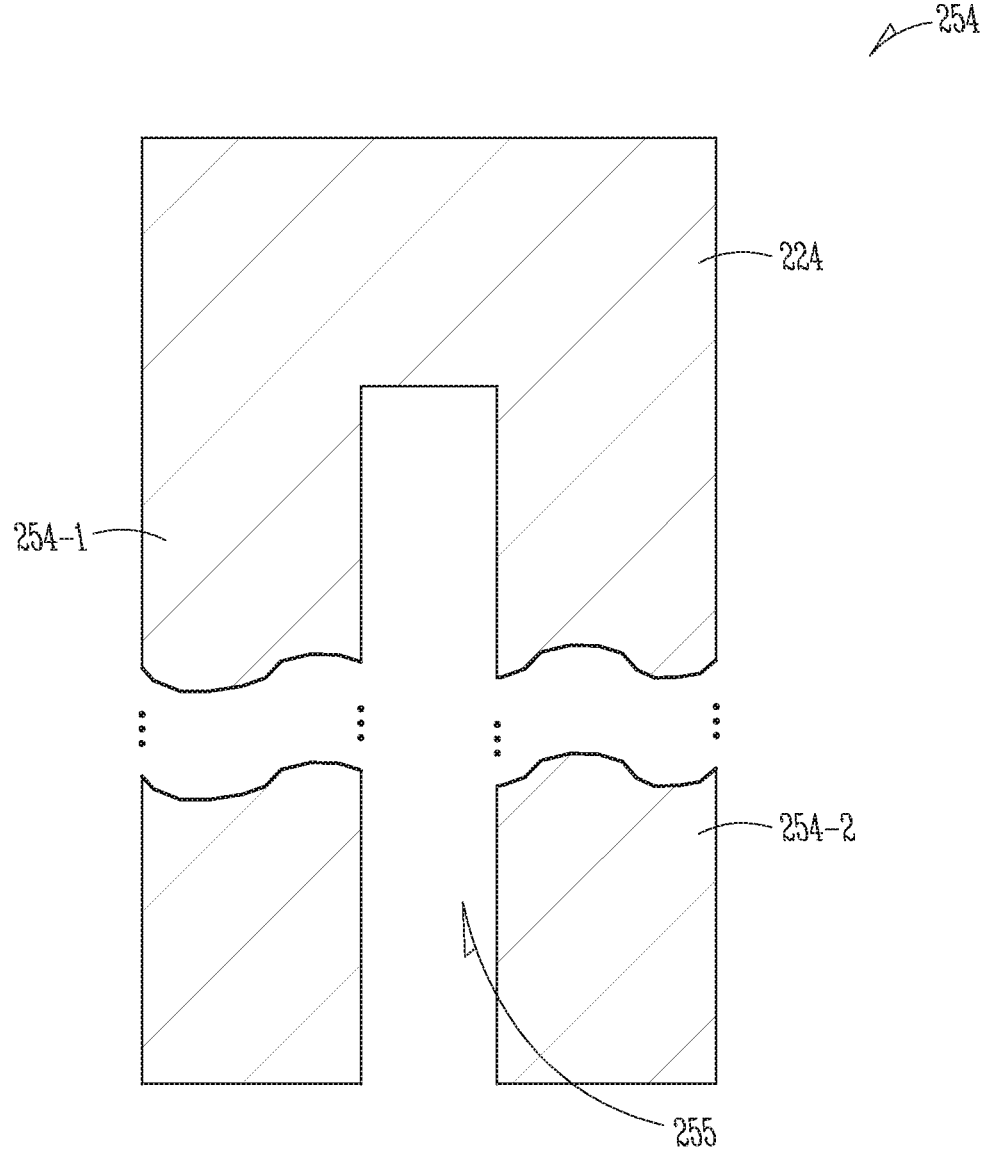
FIG. 11 is an illustrative bottom elevation view of a longitudinally extending second jaw clamping cam surface of the embodiment of FIGS. 7A-7C, in accordance with some embodiments.

FIG. 11 is an illustrative bottom elevation view of a longitudinally extending second jaw clamping cam surface 254 of the second jaw 216 in accordance with some embodiments. A bottom surface 221-1 surface of the stapler cartridge support channel structure 221 includes the second jaw clamping cam surface 254, which includes a third elongated clamping cam edge 254-1 and a parallel fourth cam edge 254-2 that run on opposite sides of and parallel to the second elongated slot 255. A distal cross member 278-1 interconnects the third and fourth edges 254-1, 254-2. The cross-beam portion 258 slides within the second elongated slot 255 with the second inward facing surface 262-1 of the second transverse beam portion 262 contacting the cam edges 254-1, 254-2. Moreover, in accordance with some embodiments, the third tubular guide channel 105-3 is laterally spaced apart from the second elongated slot 255 by the same amount, e.g., $D_1$, that the first and second tubular guide channels are spaced apart from the first elongated slot 253.

FIG. 12 is an illustrative side perspective view of the first jaw 214 showing the jaw-mounted pulley 103 and the first transverse beam portion 260 of the cable driven slider beam 104 in accordance with some embodiments. The outer first jaw cover 251 is not shown in order to show components underneath it. FIG. 13 is an illustrative perspective view showing the first jaw 214 with the first transverse beam portion 260 is shown with dashed lines to indicate the passage of portions of the first cable segment 110 within the first and second tubular guide channels 105-1, 105-2. The second transverse beam portion 262 is shown with the second cable segment 112 secured within the third tubular guide channel 105-3. The jaw-mounted pulley 103 is disposed adjacent a distal end 214-1 of the first jaw 214. The jaw-mounted pulley's axle 103-1, Shown in FIG. 10, has an axis 264 that extends perpendicular to a longitudinal axis of the first jaw 214. The first cable segment 110 wraps around the jaw-mounted pulley 103, which guides it between a slider cable routing system 106, shown in FIG. 14, and an anchor point 266 in the first tubular guide channel 105-1 defined by the first transverse beam portion 260 of the slider 104.

The first cable segment 110 extends longitudinally along a first side of the first jaw 214 above the first clamping cam edge 252-1 from the slider cable routing system 106 into the second tubular guide channel 105-2 formed in the first transverse beam member 260. The first cable segment extends 260 through the second tubular guide channel 105-2 to the jaw-mounted pulley 103. It wraps around the jaw mounted pulley 103 and extends longitudinally along a second side of the first jaw 214 above the second clamping cam edge 252-2 and into the first tubular guide channel 105-1. It is secured to the anchor point 266 within the second tubular guide channel 105-2.

The second cable segment 112 extends longitudinally along the first side of the first jaw 214 from the slider cable routing system 106 into the third tubular guide channel 105-3 formed in the second transverse beam member 262. It is secured to the anchor point 268 within the third tubular guide channel 105-3. In an alternative embodiment (not shown), the second cable segment 112 is secured to the first transverse member 260.

In operation, the proximal actuation assembly 202 selectively imparts proximal directions, forces to the first and second cables 110, 112 to alternately move the slider beam 104 longitudinally in a distal direction toward the distal ends 214-1, 216-1 of the first and second jaws 214, 216 and to move the slider beam 104 longitudinally in a proximal direction toward proximal jaw ends 214-2, 216-2 of the first and second jaws 214, 216. To move the slider beam 104 in the distal direction, the proximal actuation assembly 202 imparts a proximal direction force to the first cable segment 110 that pulls the portion of the first cable segment 110 that extends above the second clamping edge 252-2 and through the second tubular guide channel 105-2 to move in a direction toward the proximal end 214-2 of the first jaw 214 and toward the wrist 208 and the main shaft 206. During distal direction movement of the slider beam 104, a lesser proximal force is applied to the second cable segment 112 so as to not oppose the proximal force applied to the first cable 110, so as to take up slack in the second cable segment 112. The jaw-mounted pulley 103 transforms the proximal direction pulling force imparted to the portion of the first beam segment 110 that extends above the second clamping edge 252-2 and through the second tubular guide channel 105-2, to a distal direction pulling force that is applied to the portion of the first cable segment 110 that extends above the first clamping edge 252-1 and through the first tubular guide channel 105-1, where it is secured to the first transverse member 260. The distal direction pulling force imparted to the portion of the first cable segment 110 that extends above the first clamping edge 252-1 and through the first tubular guide channel 105-1, causes that portion of the first cable segment 110 and the first transverse beam 260 secured to it to move, in a longitudinal distal direction, toward the distal end 214-1 of the first jaw 214 and away from the wrist 208 and the main shaft 206.

Conversely, to move the slider beam 104 in the proximal direction, the proximal actuation assembly 202 imparts a proximal direction force to the second cable segment 112 that pulls the second cable segment 112, which extends above the third clamping edge 254-2 and into the third tubular guide channel 105-3, to which it is secured, to move the slider beam 104 in a proximal direction toward the proximal end 214-2 of the first jaw and toward the wrist 208 and the main shaft 206. During proximal direction movement of the slider beam 104, a lesser proximal force is applied to the first cable segment 110 so as to not oppose the proximal force applied to the second cable 112, so as to take up slack in the first cable segment 110.

It will be understood that the first cable segment 110 and the second cable segment 112 operate in unison. For example, during application of a proximal direction force to one portion of the first cable segment 110, resulting in movement of another portion of the first cable segment 110 and the slider beam 104 secured to it, in a distal direction, toward the distal end 214-1 of the first jaw, a tension force is applied to the second cable segment 112 that is strong enough to maintain stability while weak enough to permit the distal direction movement of the slider beam 104. Likewise, during application of a force to the second cable segment 112 resulting in movement of the slide beam 104 toward the proximal end 214-2 of the first jaw 214, a tension force is applied to the first cable 110 that is strong enough to maintain stability while weak enough to permit the proximal direction movement of the slider beam 104. U.S. Pat. No. 5,797,900 (filed May 16, 1997) issued to Madhani et al., which is incorporated herein in its entirety by this reference, discloses a use of cables and tension forces in surgical instruments. Also, in accordance with some embodiments, the second and third tubular guide channels, 105-2, 105-3 extend in parallel directions and each is transversely spaced apart by the same distance, e.g., $D_1$, from the opposite sides of the first elongated slot 253 so as to balance motions that are applied simultaneously to each.

Moreover, it is noted that in some embodiments, the respective first and second cable segments 110, 112 are secured to respective distal ends of relatively rigid elongated members (not shown), sometimes referred to as hypotubes, that extend through the length of the main shaft 206. Each elongated member typically is secured at its proximal end to a proximally located cable segment (not shown) that wraps about one or more proximal pulleys (not shown) within the proximal actuation assembly 202. U.S. Pat. No. 5,797,900 discloses the use of a relatively rigid member having cable segments at its opposite ends to achieve cable controlled control of an end effector such as a jaw assembly.

As the slider beam 104 is pulled either in a distal direction or in a proximal direction, the first and second channels 105-1, 105-2 in which the first cable segment extends act as bearing surfaces to maintain transverse spacing between portions of the first cable segment 110 disposed on opposite sides of the first elongated slot 253 and act to maintain perpendicular spacing of the first cable segment 110 from the first and second elongated clamping cam edges 252-1, 252-2.

Figure 14:
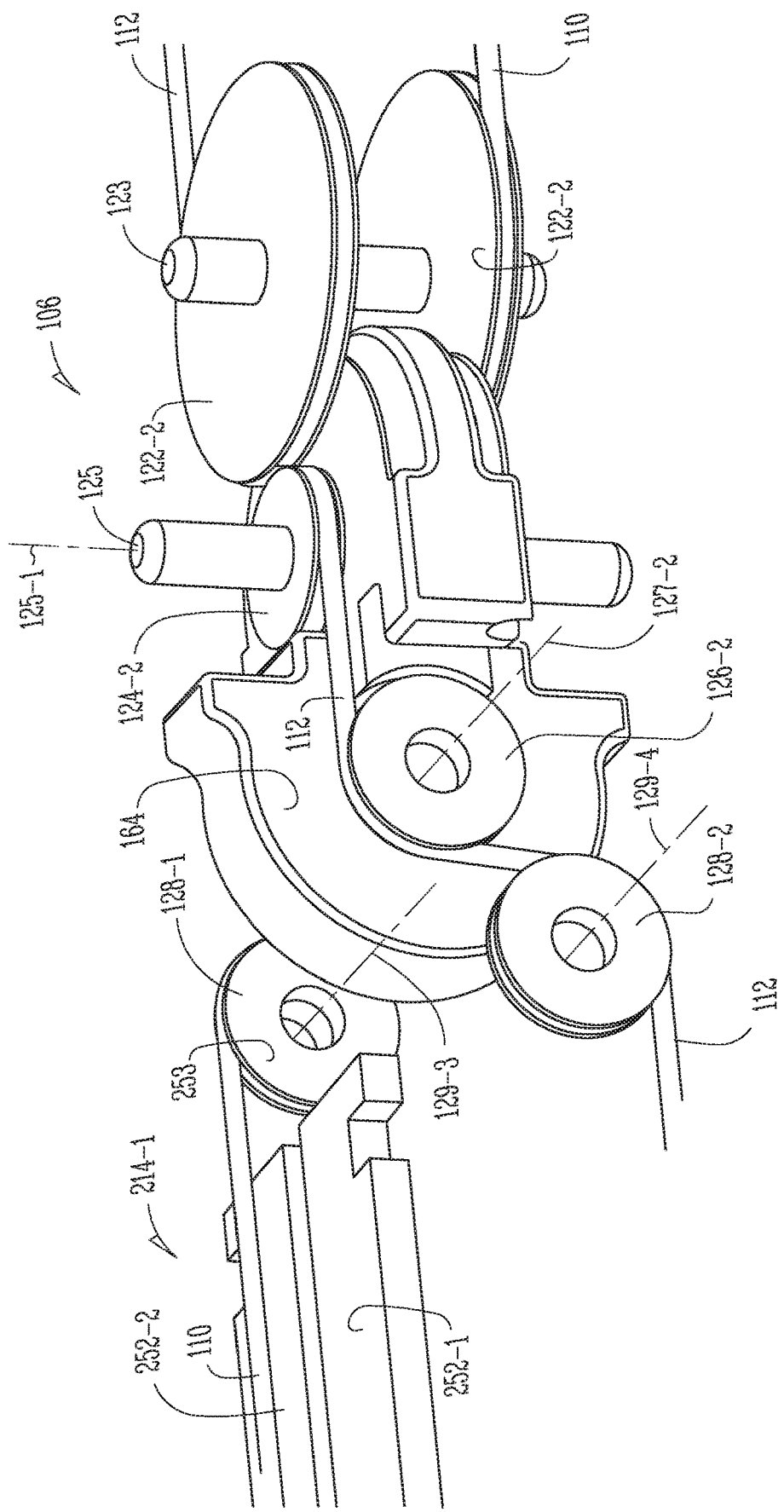
FIG. 14 is an illustrative perspective of a portion of the slider cable routing system in accordance with some embodiments.

FIG. 14 is an illustrative perspective of a portion of the slider cable routing system 106 used to route the first and second cable segments 110, 112, in accordance with some embodiments. The first and second cables 110, 112 also may be referred to herein as first and second 'slider' cables since they are used to effect movement of the slider member 104. In accordance with some embodiments, the slider cable routing system 106 is integrated with the two degree of freedom (2-dof) wrist 208, which includes a pitch cable routing system 154 described below with reference to FIG. 15, and a yaw cable routing system 136, described more fully below with reference to FIG. 17.

Referring to FIGS. 7B and to FIG. 14, the slider cable routing system 106 is disposed at the proximal end of the jaw 210. The slider cable routing system 106 routes the first cable 110 through the wrist 208, between the main shaft 206 and the first transverse beam portion 260. The slider cable routing system 106 routes the second cable 112 through the wrist 208, between the main shaft 206 and the second transverse beam portion 262. As explained more fully below, the slider cable routing system 106 routes the first and second cable segments 110, 112 through the 2-dof wrist 208 so as to conserve cable lengths. This adds two additional degrees of freedom movement to the slider member 104 that incorporates pitch and yaw motions into longitudinal slider member motion along the first jaw 214.

More specifically, the slider cable routing system 106 includes a first pair of slider idler pulleys 122-1, 122-2 mounted to a first axle 123. The slider cable routing system 106 includes a second pair of slider idler pulleys 124-1, 124-2 mounted to a second axle 125 that is aligned with a pitch axis 125-1 and that acts as a pitch axis. The slider cable routing system 106 includes a third pair of slider idler pulleys 126-1, 126-2 mounted to a third axle 127 (not shown) aligned with a yaw axis 127-1. The slider cable routing system 106 includes a fourth pair of slider idler pulleys 128-1, 128-2, respectively mounted to rotate about respective fourth and fifth slider pulley set axles (not shown), which are mounted to a proximal portion 214-1 of the first jaw 214 having axes 129-3, 129-4. The slider cable routing system 106 also includes the jaw-mounted pulley 103.

The first and second axles 123, 125 are mounted parallel to one another within a proximal clevis 130, described below with reference to FIG. 18. The first cable 110 travels an S curve path over a first pulley 122-1 of the first slider pulley pair and then over a first pulley 124-1 of the second slider pulley pair. Similarly, the second cable 112 travels an S curve path over a second pulley 122-2 of the first slider pulley pair and then over a second pulley 124-2 of the second slider pulley pair. The S curve routing contributes to maintenance of desired tensioning of the cables and reduces the risk of their derailing. In accordance with some embodiments, the paths of the first and second cable segments allow about +/−70 degrees pitch.

The third axle (not shown) aligned with yaw axis 127-1 is mounted perpendicular to the first and second axles 123, 125, within a distal clevis 126 described below with reference to FIG. 17. The first cable 110 travels a straight path between the first pulley 124-1 of the second slider pulley pair and a first pulley 126-1 of the third slider pulley pair. Similarly, the second cable 112 travels a straight path between a second pulley 124-2 (not shown) of the second slider pulley pair and a second pulley 126-2 (not shown) of the third slider pulley pair. In accordance with some embodiments, the first and second cable paths allow +/−70 degrees rotation.

The fourth and fifth slider pulley set axles 129-1, 129-2 (not shown), having axis 129-3, 129-4 respectively, are mounted parallel to the third axle, having axis 127-2, and perpendicular to the first and second axles 123, 125. The first cable 110 travels an S curve path over the first pulley 126-1 (not shown) of the third slider pulley pair and then over a first pulley 128-1 of the fourth slider pulley pair. The second cable 112 travels an S curve path over a second pulley 126-2 of the third slider pulley pair and then over a second pulley 128-2 of the fourth slider pulley pair.

Proximal end portions of the first and second jaws 214, 216 are mounted to move in a yaw rotation about the third axle 127. The fourth and fifth slider pulley set axles 129-1, 129-2, and the pulleys 128-1, 128-2 are mounted to move in unison with yaw motion of the first and second jaws 214, 216 during pivoting of the jaws 214, 216 about the third axle 127. Thus, yaw rotation imparted by the wrist 208 also is imparted to the pulleys of the slider cable routing system 106.

Moreover, the first and second pulleys 128-1, 128-2 of the fourth slider pulley pair are offset from each other by a fixed amount in a direction perpendicular to the longitudinal axis of the first jaw 102-1. More particularly, the first and second pulleys 128-1, 128-2 of the fourth slider pulley pair are offset from each other such that the first cable 110 extends in a straight path between the first pulley 128-1 of the fourth slider pulley pair and the second tubular guide channel 105-2 defined by the first transverse beam portion 260, and such that the second cable 112 extends in a straight path between the second pulley 128-2 of the fourth slider pulley pair and the third tubular guide channel 105-3 defined by the second transverse beam portion 262.

Figure 15:
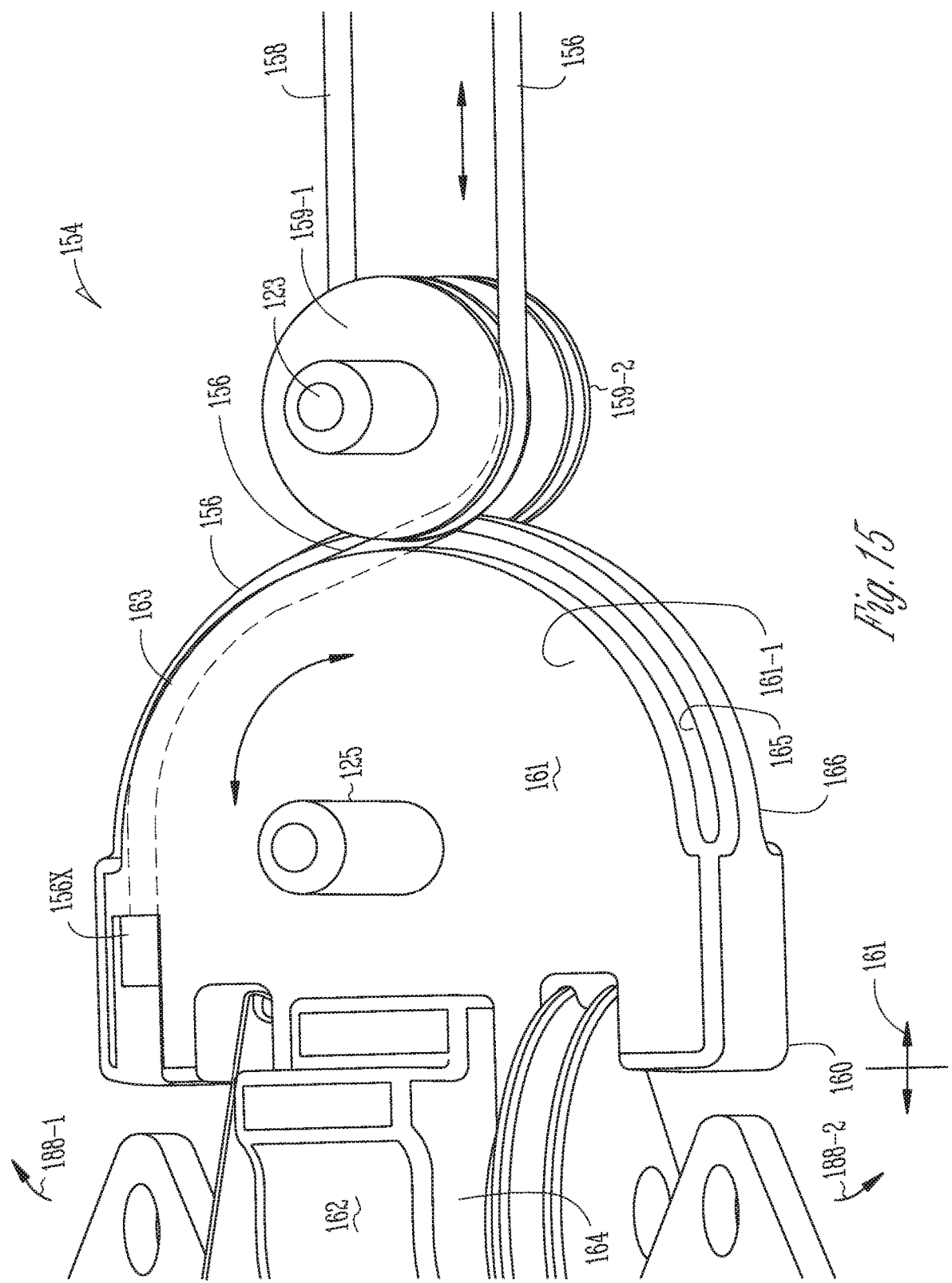
FIG. 15 is an illustrative perspective view of a pitch cable routing system in accordance with some embodiments.

FIG. 15 is an illustrative perspective view of a pitch cable routing system 154 used to route the third and fourth cable segments 156, 158, between the main shaft 206 and the jaw assembly 210, in accordance with some embodiments. The pitch cable routing system 154 is a portion of the 2-dof wrist 208. The third and fourth cables 156, 158 also may be referred to as third and fourth 'pitch' cables since they are used to achieve a pitch movement of the jaw assembly 210. The pitch cable routing system 154 routes the third cable 156 between the main shaft 206 and a rotatably mounted dual axle support member 160. The pitch cable routing system 154 includes a pair of idler pitch pulleys 159-1, 159-2, which are mounted on the first axle 123. The pitch cable routing system 154 also includes the dual axle support member 160, which is rotatably mounted on the second axle 125, also referred to herein as a pitch axle.

Figure 16A:
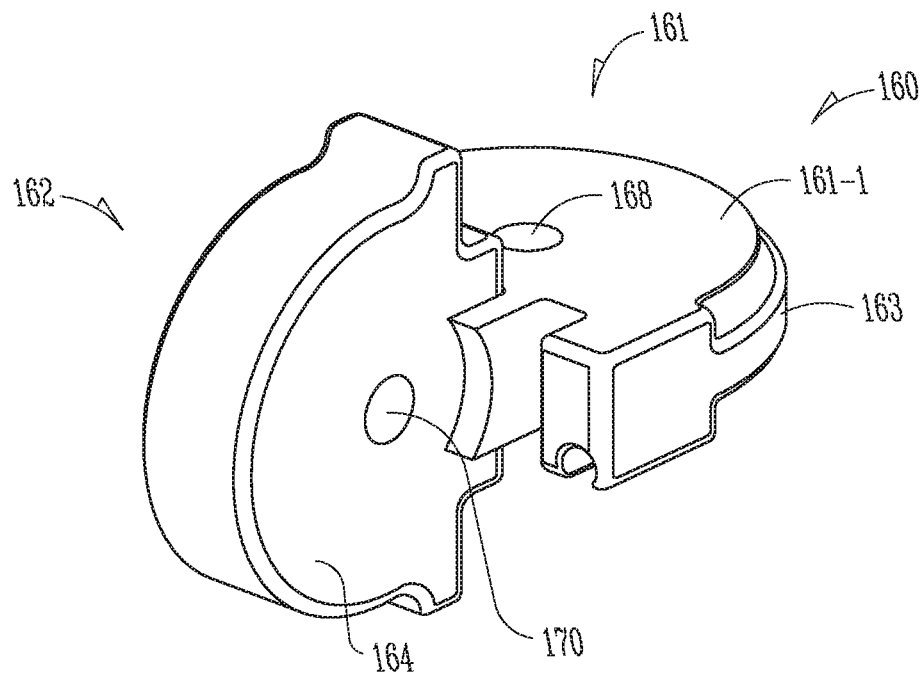
FIG. 16A is an illustrative distal perspective view of a dual axle support member in accordance with some embodiments.
Figure 16B:
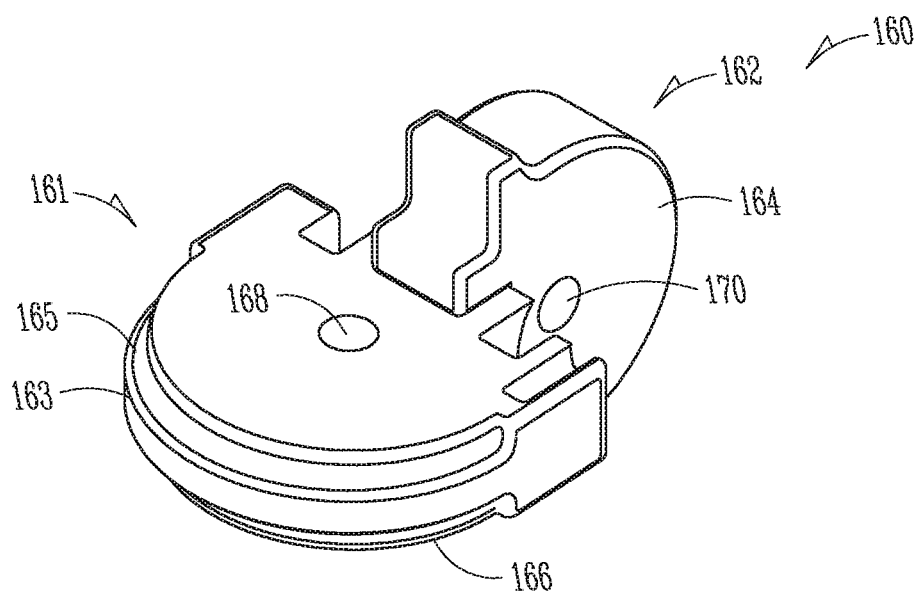
FIG. 16B is an illustrative proximal perspective view of the dual axle support member in accordance with some embodiments.

FIG. 16A is an illustrative distal perspective view of a dual axle support member 160 in accordance with some embodiments. FIG. 16B is an illustrative proximal perspective view of the dual axle support member 160 in accordance with some embodiments. The dual axle support member 160 includes a proximal side 161 and a distal side 162. The proximal side 161 includes first and second oppositely facing surfaces 161-1, 161-2 (only one shown) and has a proximal-facing semi-circular peripheral contour portion 163 having a center bore 168 sized to receive and rotate about the second axle 125, which acts as the pitch axle. the proximal side 161 defines a semi-circular partial pulley 163 having a first perimeter groove 165 adjacent the first proximal side surface 161-1 that is sized to receive a portion of the third cable segment 156 and that follows the semi-circular contour adjacent the first surface 161-1. The partial pulley 163 also has a second perimeter groove 166 adjacent the second surface (not shown) that is sized to receive a portion of the fourth cable segment 158.

The distal side 162 includes a distally extending third axle support arm 164 that defines a bore 170 transverse to the axis of the second axle 125 that is sized to rotatably mount the third (yaw) axle (not shown) therein. As explained elsewhere herein, the third axle, the yaw axle 127 is rotatably mounted within the bore 170 defined by the distally extending third axle support arm 164 and extends perpendicular to the second axis 125 for mounting the slider idler pulleys 126-1, 126-2 and for mounting yaw idler pulleys 152-1 (not visible), 152-2.

Referring again to FIG. 15, the third cable 156 travels an S curve path between a first idler pitch pulley 159-1 of the idler pitch pulley pair and the first perimeter groove 165. A distal end of the third cable is secured to one end of the first perimeter groove. Similarly, the fourth cable 158 travels an S curve path between a second idler pitch pulley 159-2 of the pitch pulley pair and the second perimeter groove 166. A distal end of the fourth cable 158 is secured to one end of the second perimeter groove 166. The ends of the first and second grooves where the respective ends of the third and fourth cables are secured are diametrically opposite to one another. In accordance with some embodiments, the fifth and sixth cable paths allow about +/−70 degrees rotation.

Using FIG. 15 as a reference, in operation in accordance with some embodiments, pulling in a proximal direction on the third cable 156 causes the dual axle support member 160 to rotate in a clockwise direction about the second axle 125. Conversely, pulling in a proximal direction on the fourth cable 158 causes the dual axle support member 160 to rotate in a counter-clockwise direction about the second axle 125. It will be appreciated that the slider cable routing system 106 also shares use of the second axle 125. The slider cable routing system 106 thereby effects longitudinal motion of the slider beam 104 in accordance with pitch orientation of the first jaw 214 effected using the pitch cable routing system 154.

A distal portion of the third cable segment 156 wraps about and is secured, via crimp 156X, within the first perimeter groove 165 of the partial pulley 163, which is rotatably mounted on the pitch axle 125, such that a proximal force applied to the third cable segment 156 causes (clockwise) rotation of the jaw assembly 210 as indicated by arrow 188-1. More particularly, as the third cable 156 moves in a proximal direction, it rotates the partial pulley 163 about the pitch axle 125. During provision of a proximal force to the third cable segment 156, a proximal force is applied to the fourth cable segment 158 so as to retract it proximally without resisting the proximal force applied to the third cable segment 156.

Similarly, a distal portion of the fourth cable segment 158 wraps about and is secured, via crimp 158X, within the second perimeter groove 166 of the partial pulley 163, which is rotatably mounted on the pitch axle 125, such that a proximal force applied to the fourth cable segment 158 causes (counter-clockwise) rotation of the jaw assembly 210 as indicated by arrow 188-2. More particularly, as the fourth cable 158 moves in a proximal direction, it rotates the partial pulley 163 about the pitch axle 125. During provision of a proximal force to the fourth cable segment 158, a proximal force is applied to the third cable segment 156 so as to retract it proximally without resisting the proximal force applied to the fourth cable segment 158.

Figure 17:
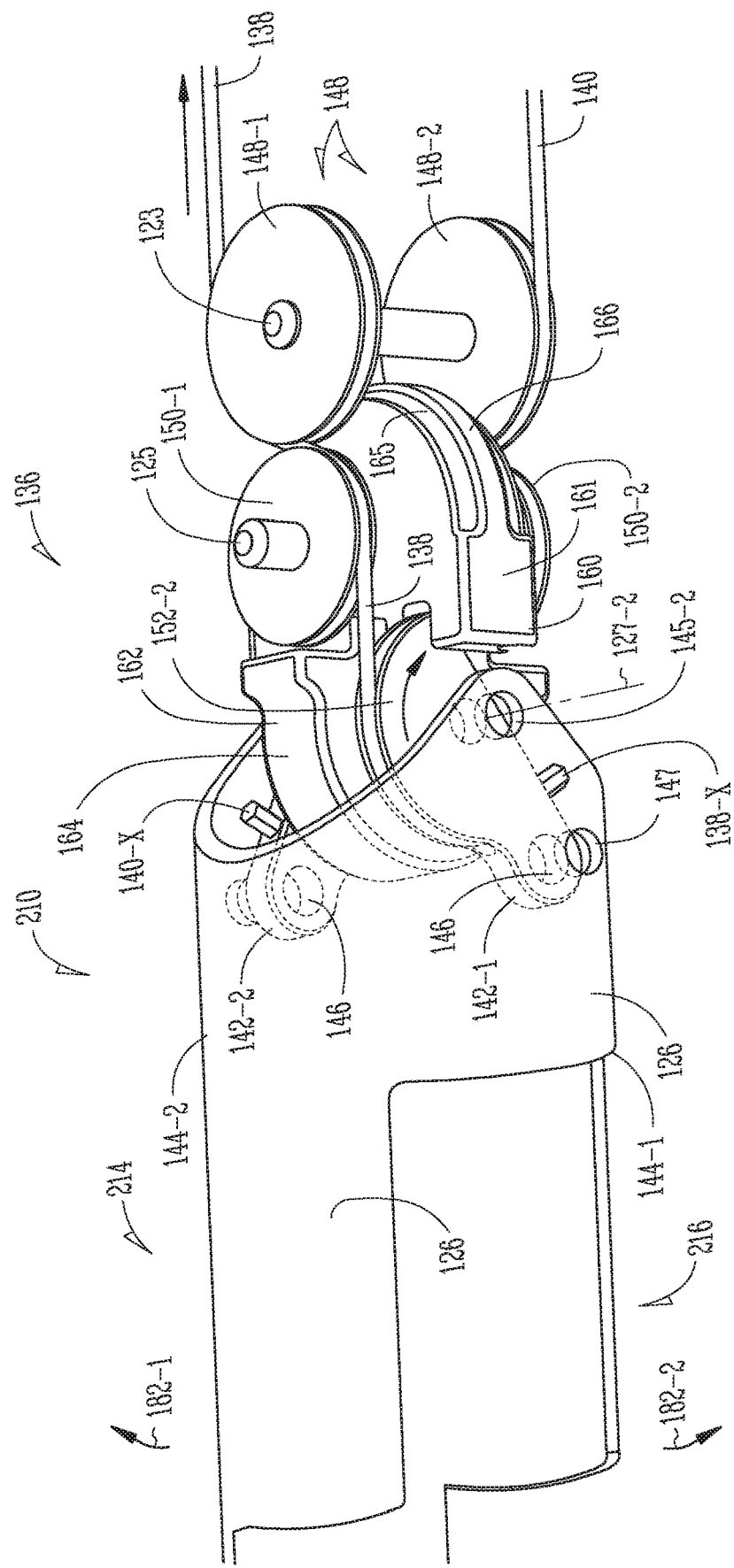
FIG. 17 is an illustrative perspective view of a yaw cable routing system in accordance with some embodiments.

FIG. 17 is an illustrative perspective view of a yaw cable routing system 136 used to route the fifth and sixth cable segments 138, 140, between the main shaft 206 and the jaw assembly 210, in accordance with some embodiments. The yaw cable routing system 136 is a portion of the 2-dof wrist 208. Proximal portions of the first and second jaws 214, 216 are shown transparent, using dashed lines, to show their physical relationship with the yaw cable routing system 136. The fifth and sixth cables 138, 140 also may be referred to as fifth and sixth 'yaw' cables since they are used to achieve a yaw movement of the jaw assembly 210.

The yaw cable routing system 136 includes a first yaw pulley set 148 that includes a first pair of yaw idler pulleys 148-1, 148-2 mounted to the first axle 123. The yaw cable routing system 136 includes a second pair of yaw idler pulleys 150-1, 150-2 mounted to the second axle 125. The yaw cable routing system 136 includes a third pair of yaw partial pulleys 152-1, 152-2 (not visible) mounted to the third axle 127 (not shown). The fifth (yaw) cable 138 travels an S curve path over a first pulley 148-1 of the first yaw pulley pair and then over a first pulley 150-1 of the second yaw pulley pair. Similarly, the sixth (yaw) cable 140 travels an S curve path over a second yaw idler pulley 148-2 of the first yaw pulley set and then over a second yaw idler pulley 150-2 of the second yaw pulley set. The fifth cable 138 travels a straight path between the first pulley 150-1 of the second yaw pulley pair and a first pulley 152-1 of the third yaw pulley pair. Similarly, the sixth cable 140 travels a straight path between the second pulley 150-2 of the second yaw pulley pair and a second pulley 152-2 of the third yaw pulley pair. In accordance with some embodiments, the paths of the fifth and sixth cable segments allow about +/−70 degrees rotation.

The proximal base 212 of the jaw assembly 210 includes first and second sidewalls 144-1, 144-2 that act as a distal clevis 126. The first and second sidewalls 144-1, 144-2 define a pair of opposed first and second sidewall openings 145-1, 145-2 (only one shown) that include bearing surfaces to receive opposite ends of the third (yaw) axle (not shown). The support arm 164 is received between the first and second sidewalls 144-1, 144-2 with the third axle (not shown) extending through the bore 170 and with opposite ends of the third axle supported on bearing surfaces of the first and second sidewall openings 145-1, 145-2. A first reaction arm 142-1 is formed integrally with and extends distally from the first pulley 152-1 of the third yaw pulley pair, which is rotatably mounted on the third (yaw) axle (not shown). Bores 146 formed in distal ends of the first reaction arms 142-1, 142-2 are aligned with third sidewall openings 147 in the first and second sidewalls 144-1, 144-2. The first and second reaction arms 142-1, 142-2 are secured to first and second sidewalls 144-1, 144-2 by fasteners (not shown) extending through the aligned bores 146 and sidewall openings 147. The fifth slider pulley axle 129-2 (not shown), which is aligned with axis 129-4 and has the second pulley 128-2 of the fourth slider pulley pair rotatably mounted thereon, extends through the second and fourth sidewall openings 145-2, 147. The fourth slider pulley axle 129-1 (not shown), which is aligned with axis 129-3 and has the first pulley 128-1 of the fourth slider pulley pair rotatably mounted thereon, extends through the first and third sidewall openings 145-1, 147.

A distal portion of the fifth cable segment 138 wraps about and is secured, via crimp 138X, to the first pulley 152-1 of the third yaw pulley pair, which is rotatably mounted on the third (yaw) axle, such that a proximal force applied to the fifth cable 138 causes upward (clockwise) rotation of the jaw assembly 210 as indicated by arrow 182-1. More particularly, as the fifth cable 138 moves in a proximal direction, it rotates the pulley 152-1 about the yaw axis 127-2. The first and second reaction arms 142-1, 142-2, which are secured to first and second sidewalls of the jaw assembly 210 rotate about the yaw axis 127-2 in unison with the pulley 152-1, thereby causing upward (clockwise) rotation of the jaw assembly 214 relative to the wrist 208. During provision of a proximal force to the fifth cable segment 138, a proximal force is applied to the sixth cable segment 140 so as to retract it proximally without resisting the proximal force applied to the fifth cable segment 138. It will be appreciated that movement directions such as upward, downward, clockwise and counter-clockwise are provided for convenience of description relative to the illustrative drawings and are not intended to be limiting.

Similarly, a distal portion of the sixth cable segment 140 wraps about and is secured, via crimp 140X (not visible), to the second pulley 152-2 of the third yaw pulley pair, which is rotatably mounted on the third (yaw) axle, such that a proximal force applied to the sixth cable 140 causes downward (counter-clockwise) rotation of the jaw assembly 210 as indicated by arrow 182-2. The sixth cable segment 140 wraps about the second pulley 152-2 in a direction opposite of the direction in which the fifth cable segment 138 wraps about the first pulley 152-1. More particularly, as the sixth cable 140 moves in a proximal direction, it rotates the pulley 152-2 about the yaw axis 127-2. The first and second reaction arms 142-1, 142-2, which are secured to first and second sidewalls 144-1, 144-2 of the jaw assembly 210 rotate about the yaw axis 127-2 in unison with the pulley 152-2, thereby causing upward (clockwise) rotation of the jaw assembly 214 relative to the wrist 208. During provision of a proximal force to the sixth cable segment 140, a proximal force is applied to the fifth cable segment so as to retract it proximally without resisting the proximal force applied to the sixth cable segment 140.

The first and second reaction arms 142-1, 142-2 are offset from each other in a direction perpendicular to the longitudinal axis of the first jaw 102-1 so that the slider pulleys 128-1, 128-2 mounted thereon are offset as described above to position the slider pulleys 128-1, 128-2, to guide the first and second slider cable segments 110, 112 in a linear path between the 2dof wrist and the first and second cross beam segments 260, 262, respectively, regardless of pitch and yaw orientation of the jaw assembly 210.

Figure 18:
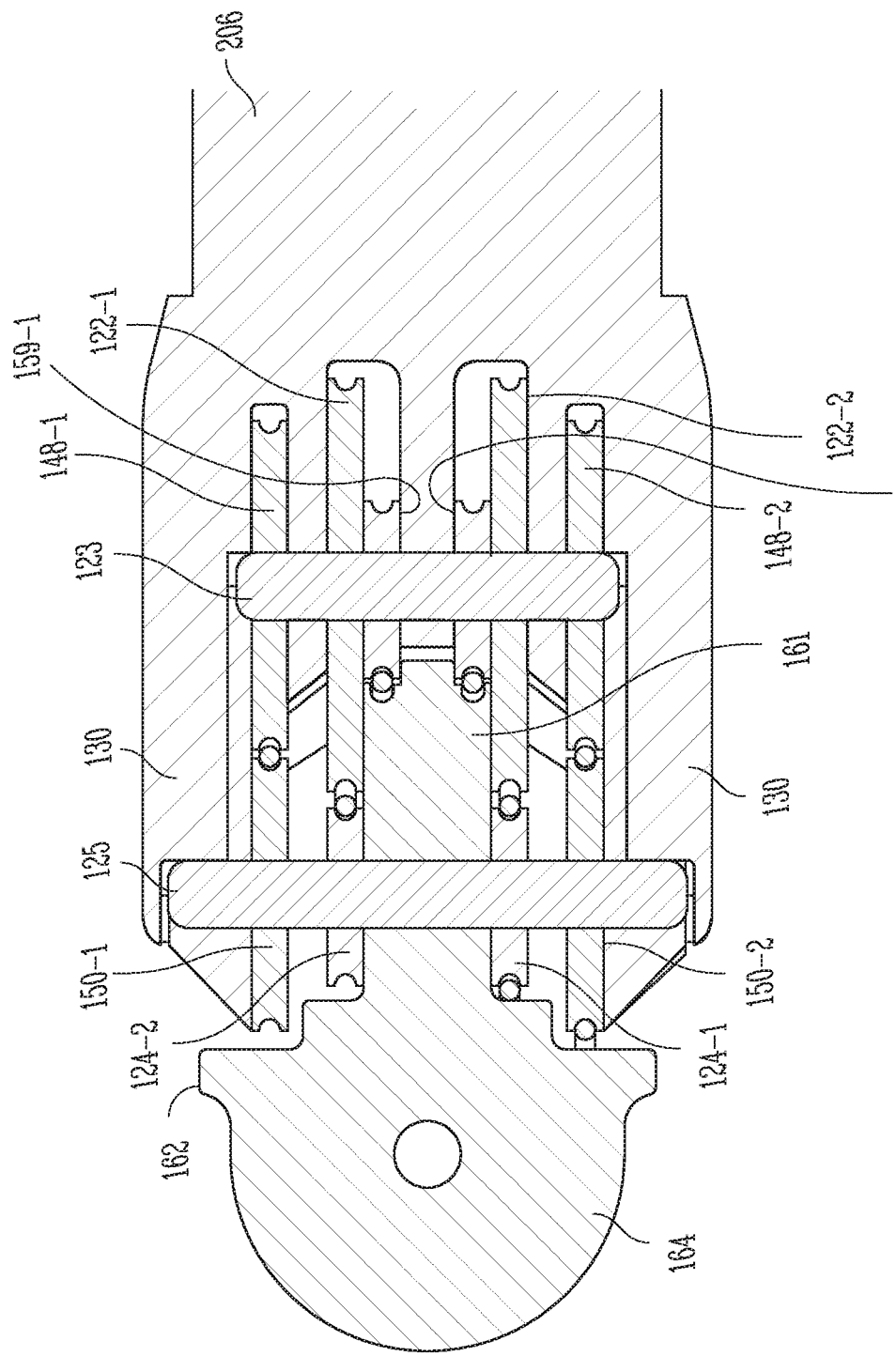
FIG. 18 is a cross-sectional side view of a proximal clevis rotatably mounting the first axle and the second axle and also mounting the slider beam, pitch and yaw cable routing system components, in accordance with some embodiments.
Figure 19:
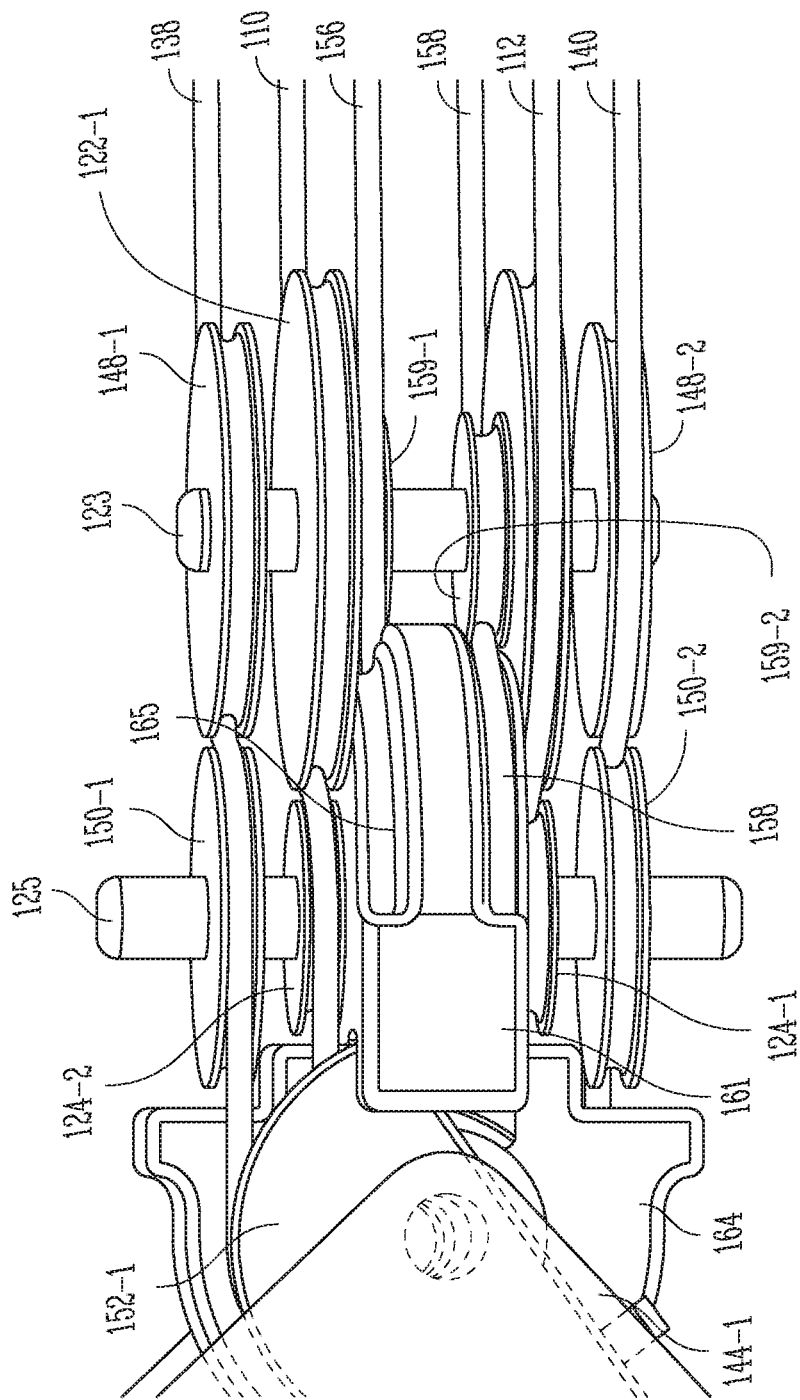
FIG. 19 is a side perspective view of the components of the slider beam, pitch and yaw cable routing systems of FIG. 18 in accordance with some embodiments.

FIG. 18 is a cross-sectional side view of a proximal clevis 130, which extends from a distal end of the main shaft 206 and rotatably mounts the first axle 123 and the second axle 125 and also mounting components of the slider beam, pitch and yaw cable routing systems 106, 154, 136, in accordance with some embodiments. Cable segments are not shown in FIG. 18 in order to simplify the drawing. FIG. 19 is a side perspective view of the components of the slider beam, pitch and yaw cable routing systems 106, 154, 136 of FIG. 18 in accordance with some embodiments. FIG. 14 also shows a portion of the sidewall 144-1 shown transparent, using dashed lines, also is shown.

Referring to FIGS. 18-19, the first pair of yaw idler pulleys 148-1, 148-2 are mounted outer-most on the first axle 123. The first pair of pitch idler pulleys 159-1, 159-2 are mounted inner-most on the first axle 123. The first pair of slider idler pulleys 122-1, 122-2 are mounted on the first axle 123 between the first yaw pair idler pulleys and the first pair of pitch idler pulleys. The second pair of yaw idler pulleys 150-1, 150-2 are mounted outer-most on the second axle 125. The second pair of slider idler pulleys 124-1, 124-2 are mounted inner-most on the second axle 125. The dual axle support member 160 is mounted on the second axle 125 between the second pair of yaw idler pulleys and the second pair of slider idler pulleys.

The foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. A surgical tool comprising:
 a jaw assembly that includes first and second elongated jaws, each elongated jaw having a proximal end and a distal end, wherein the proximal end of the first elongated jaw is mounted to be rotatable about a pivot axis between an open position and a closed position;
 first parallel side edges secured to the first elongated jaw that extend parallel to a longitudinal first axis of the first elongated jaw;
 second parallel side edges secured to the second elongated jaw that extend parallel to a longitudinal second axis of second elongated jaw;
 a slider beam that includes a cross-beam portion sized to slidably fit between the first parallel side edges and between the second parallel side edges, a first transverse beam configured to slidably engage surfaces of the first parallel side edges facing away from the second elongated jaw, and a second transverse beam configured to slidably engage surfaces of the second parallel side edges facing away from the first elongated jaw;
 a pulley rotatably mounted to the distal end of the first elongated jaw ; and
 a first slider cable secured to the first transverse beam, the first slider cable extending from a distal side of a portion of the first transverse beam that engages one of the first parallel side edges, extending about the pulley, extending through a channel formed in a portion of the first transverse beam that engages another of the first parallel side edges, and extending to the proximal end of the first elongated jaw;
 wherein the pulley is rotatably mounted to transform a first proximal direction pulling force applied to a portion of the first slider cable that extends through the channel to the proximal end of the first elongated jaw into a distal direction pulling force upon a portion of the first slider cable secured to the first transverse beam; and
 a second slider cable secured to the one of the first and second transverse beams and extending between the one of the first and second transverse beams and the proximal end of the second elongated jaw;
 wherein the second slider cable is secured to the one of the first and second transverse beams such that a proximal direction pulling force applied to the second slider cable imparts proximal direction pulling force upon the one of the first and second transverse beams.

2. The surgical tool of claim 1,
wherein the proximal ends of the first and second elongated jaws are releasably secured to each other.

3. The surgical tool of claim 1,
wherein the jaw assembly includes a base; and
wherein the proximal end of the first elongated jaw is rotatably mounted to the base.

4. The surgical tool of claim 1,
wherein the pulley is rotatably mounted to rotate about a pulley axis perpendicular to the longitudinal first axis.

5. The surgical tool of claim 1 further including:
a shaft that includes a proximal end portion and a distal end portion; and
a two degree of freedom wrist coupling the jaw assembly to the distal end portion of the shaft.

6. The surgical tool of claim 5 further including:
a slider cable routing system to route the first slider cable through the two degree of freedom wrist between the shaft and the first transverse beam and to route the second slider cable through the two degree of freedom wrist between the shaft and the one of the first and second transverse beams.

7. The surgical tool of claim 6 further including:
wherein the two degree of freedom wrist includes a pitch cable routing system to route first and second pitch cables between the shaft and jaw assembly;
wherein the two degree of freedom wrist includes a yaw cable routing system to route first and second yaw cables between the shaft and the pitch cable routing system.

8. The surgical tool of claim 5,
wherein the two degree of freedom wrist includes a pitch cable routing system to route first and second pitch cables between the shaft and a member that is secured to the jaw assembly and that is rotatable about a pitch axis;
wherein the two degree of freedom wrist includes a yaw cable routing system to route first and second yaw cables between the shaft and a member that is secured to the jaw assembly and that is rotatable about a yaw axis; further including:
a slider cable routing system to route the first slider cable, around the pitch axis, around the yaw axis, between the shaft and the first transverse beam and to route the second slider cable, around the pitch axis, around the yaw axis, between the shaft and the one of the first and second transverse beams.

9. The surgical tool of claim 1 further including:
a staple cartridge disposed in the second elongated jaw and defining a longitudinal slot in which the slider beam cross-beam portion slidably fits.

10. The surgical tool of claim 1 further including:
a staple cartridge disposed in the second elongated jaw and defining a longitudinal slot in which the slider beam cross-beam portion slidably fits; and
a staple pusher slidably mounted within the staple cartridge for movement a longitudinal axis of the second elongated jaw;
wherein the slider beam cross-beam portion is disposed to push the staple pusher in a distal direction within the staple cartridge during distal direction movement of the slider beam within the channel.

11. The surgical tool of claim 10,
wherein the slider beam includes a knife portion.

12. The surgical tool of claim 1 further including:
a slider cable routing system to route the first slider cable through a wrist between a shaft and the first transverse beam and to route the second slider cable through the wrist between the shaft and one of the first and second transverse beams;
a staple cartridge disposed in the second elongated jaw and defining a longitudinal slot in which the slider beam cross-beam portion slidably fits; and
a staple pusher slidably mounted within the cartridge for movement along the longitudinal second axis of the second elongated jaw;
wherein the slider beam cross-beam portion is disposed to push the staple pusher in a distal direction within the cartridge during distal direction movement of the slider beam within the channel.

13. The surgical tool of claim 1 further comprising:
a shaft that includes a proximal end portion and a distal end portion; and
a two degree of freedom wrist coupling the jaw assembly to the distal end portion of the shaft.

14. The surgical instrument of claim 13 further including:
a slider cable routing system to route the first slider cable through the two degree of freedom wrist between the shaft and the first transverse beam and to route the second slider cable through the two degree of freedom wrist between the shaft and the one of the first transverse beam;
a staple cartridge disposed in the second elongated jaw and defining a longitudinal slot in which the slider beam cross-beam portion slidably fits; and
a staple pusher slidably mounted within the cartridge for movement along the longitudinal second axis of the second elongated jaw.

\* \* \* \* \*

UNITED STATES PATENT AND TRADEMARK OFFICE
CERTIFICATE OF CORRECTION

PATENT NO. : 10,631,858 B2
APPLICATION NO. : 15/433101
DATED : April 28, 2020
INVENTOR(S) : William A. Burbank Page 1 of 1

It is certified that error appears in the above-identified patent and that said Letters Patent is hereby corrected as shown below:

In the Claims

In Column 16, Line 45, in Claim 1, delete "jaw ;" and insert --jaw;-- therefor

In Column 18, Line 10, in Claim 10, after "movement", insert --along--

Signed and Sealed this
Ninth Day of June, 2020

Andrei Iancu
*Director of the United States Patent and Trademark Office*